(12) United States Patent
Zhang et al.

(10) Patent No.: US 10,759,802 B2
(45) Date of Patent: Sep. 1, 2020

(54) COMPOUND, PREPARATION METHOD THEREOF AND ORGANIC LIGHT EMITTING DISPLAY DEVICE

(71) Applicant: SHANGHAI TIANMA AM-OLED CO., LTD., Shanghai (CN)

(72) Inventors: Zhengchuan Zhang, Wuhan (CN); Hao Dai, Shanghai (CN); Defeng Bi, Shanghai (CN)

(73) Assignee: SHANGHAI TIANMA AM-OLED CO., LTD., Shanghai (CN)

( * ) Notice: Subject to any disclaimer, the term of this patent is extended or adjusted under 35 U.S.C. 154(b) by 341 days.

(21) Appl. No.: 15/803,833

(22) Filed: Nov. 5, 2017

(65) Prior Publication Data

US 2018/0099968 A1    Apr. 12, 2018

(30) Foreign Application Priority Data

May 17, 2017    (CN) .......................... 2017 1 0348953

(51) Int. Cl.
| | | |
|---|---|---|
| *C07D 471/20* | (2006.01) | |
| *H01L 51/00* | (2006.01) | |
| *C09K 11/06* | (2006.01) | |
| *H01L 51/52* | (2006.01) | |
| *H01L 51/50* | (2006.01) | |

(52) U.S. Cl.
CPC ............ *C07D 471/20* (2013.01); *C09K 11/06* (2013.01); *H01L 51/0003* (2013.01); *H01L 51/0056* (2013.01); *H01L 51/0072* (2013.01); *H01L 51/5203* (2013.01); *H01L 51/5012* (2013.01)

(58) Field of Classification Search
CPC ... C07D 471/20; C09K 11/06; H01L 51/0003; H01L 51/0056; H01L 51/0072; H01L 51/5012; H01L 51/5203
See application file for complete search history.

(56) References Cited

U.S. PATENT DOCUMENTS

| | | | | |
|---|---|---|---|---|
| 2003/0008174 A1* | 1/2003 | Suzuki | ................... | C09K 11/06 428/690 |
| 2008/0093980 A1* | 4/2008 | Stoessel | ................. | C07C 13/62 313/504 |
| 2013/0087529 A1* | 4/2013 | Hatakeyama | ....... | H01L 21/0271 216/47 |
| 2014/0144509 A1* | 5/2014 | Fadhel | ................... | B82Y 10/00 136/263 |
| 2014/0200350 A1* | 7/2014 | Nguyen | ................... | C08F 2/50 546/42 |

FOREIGN PATENT DOCUMENTS

CN    104835916 A    8/2015

\* cited by examiner

*Primary Examiner* — Dawn L Garrett
(74) *Attorney, Agent, or Firm* — Kilpatrick Townsend & Stockton, LLP

(57) ABSTRACT

The present disclosure relates to the field of technology of an OLED material and a device having the same, and particularly to a compound, a preparation method thereof and an organic light emitting display device, wherein the compound has a structure expressed by formula (I).

12 Claims, 6 Drawing Sheets

COMPOUND, PREPARATION METHOD THEREOF AND ORGANIC LIGHT EMITTING DISPLAY DEVICE

This application claims the benefit of Chinese Patent Application No. CN 201710348953.0, filed with the Chinese Patent Office on May 17, 2017, which is hereby incorporated by reference in its entirety.

FIELD

The present disclosure relates to the field of Organic Light Emitting Diode (OLED) materials and device having the same, and particularly to a compound, a preparation method thereof and an organic light emitting display device.

BACKGROUND

A polymer material represented by polyphenylacetylene (PPV) and polyvinyl carbazole (PVK) was applied to solution processed OLED at the earliest, which has a good solubility and excellent film-forming properties, but has disadvantages that the polymer is actually a mixture, with a molecular weight failing to be accurately controlled and poor reproducibility, and is difficult to be purified, thereby greatly affecting the device performance.

Since 2012, small molecules become new favorites for solution processing devices, and in the field of bipolar host, a "phosphorescent" spin coating device is manufacturing by vapor-depositing small molecules, so as to achieve 18.0% external quantum efficiency. But because small molecules have the problems of poor film-forming properties, easily dewetting, and fluid characteristics highly dependent on solvent, developing small molecule materials having excellent solubility, good film-forming properties and being reliable when forming devices is still a great challenge.

The technology of a solution-processable TADF (thermal active delay fluorescent) device has gradually become a hotspot since 2015. The prior art has reported an axisymmetric star-shaped soluble molecule, which has a $\Delta E_{ST}$ of only 0.02 eV and very typical TADF properties. The external quantum efficiency of spin coating devices with it as the light emitting layer is as high as 5.2%, but it is still less satisfactory in the aspects of electrical properties and film-forming properties, etc.

SUMMARY

In order to solve the above deficiencies of the prior art, the present disclosure provides a compound, a light emitting material and a device having the same, and a display device.

In one aspect according to the present disclosure, there is provided a compound having a structure expressed by formula (I),

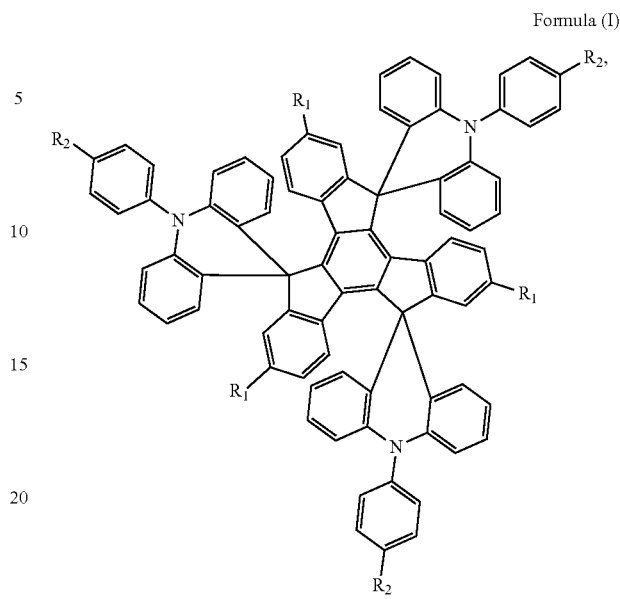

Formula (I)

$R_1$ is any one selected from halogen, —$CF_3$, —$NO_2$, —CN, phenyl, biphenyl, naphthyl, fluorenyl, triazinyl, triazolyl, tetrazolyl, benzimidazolyl, benzoxazolyl, dibenzothiophene sulfonyl, dibenzothiophenyl, pyridyl, pyrimidyl, quinolyl, isoquinolyl, substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl; $R_2$ is any one selected from a C1 to C20 linear or branched alkyl group and a C1 to C20 linear or branched alkoxy group; and substituent groups among the substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl, may be electron withdrawing groups, selected from more than one of halogen, —$CF_3$, —$NO_2$, and —CN.

In one embodiment, $R_2$ is any one selected from a C1 to C8 linear or branched alkyl group and a C1 to C8 linear or branched alkoxy group; in another embodiment, $R_2$ is any one selected from the group consisting of methyl, ethyl, propyl, isopropyl, butyl, isobutyl, sec-butyl, tert-butyl, —(CH$_2$CH$_3$)CH$_2$CH$_2$CH$_2$CH$_2$CH$_3$, methoxy, ethoxy, propoxy, isopropoxy, butoxy, isobutoxy, sec-butoxy and tert-butoxy.

In the structure of the present disclosure, three triphenylamines are used as donor units, cyanotruxenone is used as an acceptor unit, and the N-4' site of the triphenylamine is bound to R$_2$ for hydrotropy.

In some embodiments, R$_1$ is any one selected from the group consisting of:

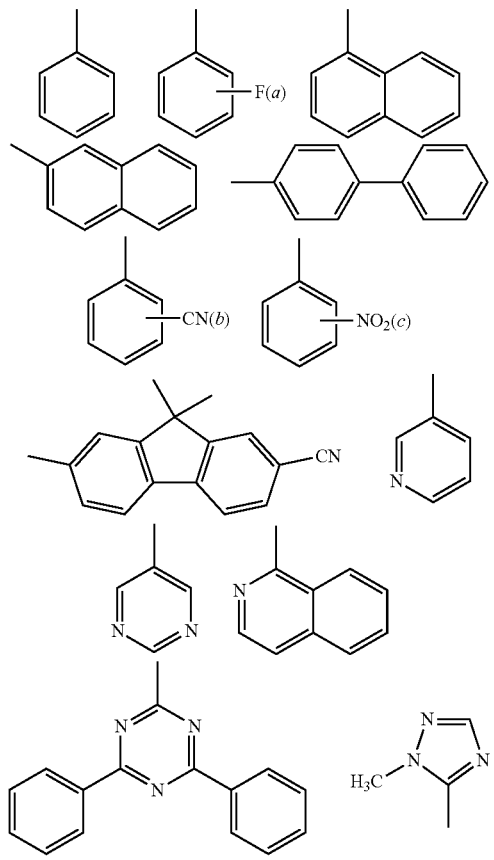

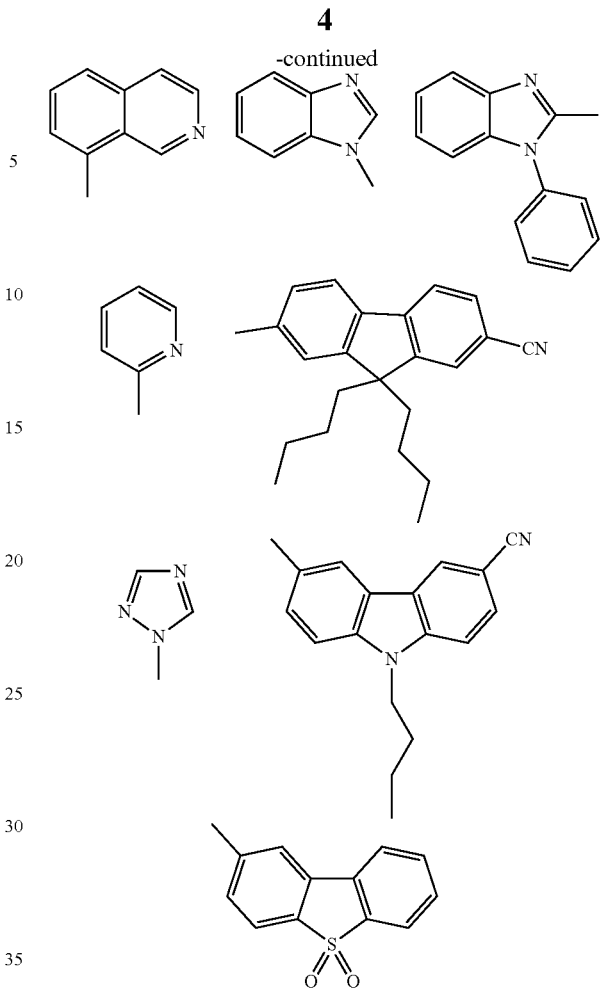

and —CN, in which a, b and c are respectively an integer independently selected from 1 to 5.

In some embodiments, the compound is expressed by formula (II),

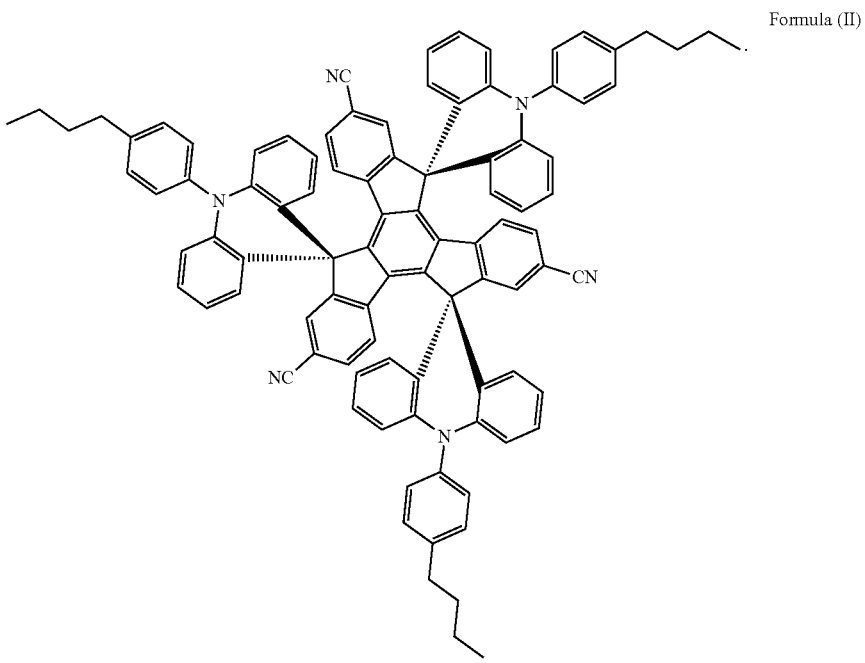 [SMILES: CCCCc1ccc(N2c3ccccc3[C@]3(c4cc(C#N)ccc4-c4c3c3c(c5c4[C@]4(c6cc(C#N)ccc6-5)c5ccccc5N(c5ccc(CCCC)cc5)c5ccccc54)[C@]4(c5cc(C#N)ccc5-3)c3ccccc3N(c3ccc(CCCC)cc3)c3ccccc34)c3ccccc32)cc1]

Formula (II)

In another aspect according to the present disclosure, there is provided a preparation method of the compound as mentioned above, including the following steps:

obtaining the compound expressed by formula (I) through a condensation reaction of a compound expressed by formula (III) and a compound expressed by formula (IV).

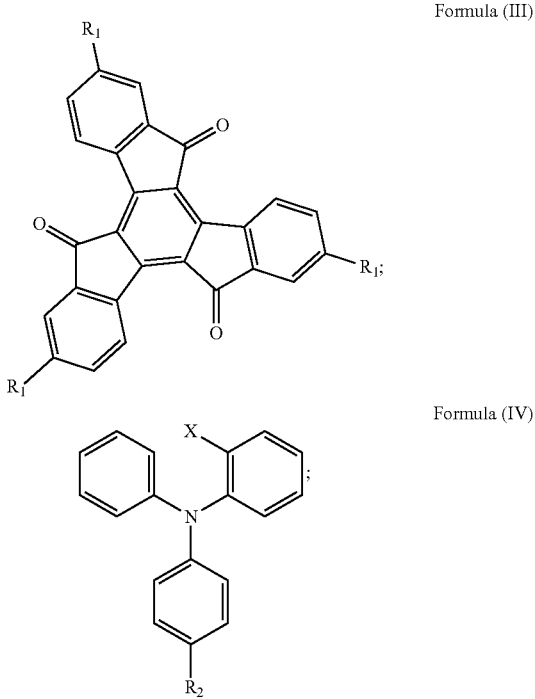

Formula (III)

Formula (IV)

X is any one selected from halogen, for example, bromine.

Preparing truxenone by using a raw material of 1,3-indandione, and obtaining the compound expressed by formula (III) through a substitution reaction.

The preparation method of the compound in the present disclosure, the target product can be obtained through substitution and condensation of the simplest raw material of 1,3-indandione, and the route thereof is simple, environmentally friendly and cheap.

In another aspect according to the present disclosure, there is provided an organic light emitting display device, including an organic electroluminescent device which includes: an organic functional layer, including one or more organic film layers, and at least one of the organic film layers is a light emitting layer; and the light emitting layer includes a light emitting material including the compound as mentioned above.

The organic electroluminescent device further includes: a base; a first electrode arranged on the base; and a second electrode arranged on the organic functional layer, and the organic functional layer is arranged on the first electrode.

In some embodiments, the light emitting material is a blue thermally activated delayed fluorescence material.

In some embodiments, the light emitting material is a host material or a guest material of the light emitting layer. When the light emitting material is used as the host material of the light emitting layer, the guest material is selected from the group consisting of 4,4'-bis(9-ethyl-3-carbazole vinyl)-1,1'-biphenyl (BczVBi), coumarin-6, and 4-(dicyanovinyl)-2-tert-butyl-6-(1,1,7,7-tetramethylguanylidene-4-vinyl) (DCJTB), etc.; and when the light emitting material is used as the guest material of the light emitting layer, the host material is selected from polyvinyl carbazole (PVK) and polyfluorene (PFO).

The organic functional layer according to the present disclosure further comprises a hole injection layer, a hole transport layer, an electron transport layer and an electron injection layer.

In some embodiments, the organic electroluminescent device is manufactured using a solution processing method.

Preparation of a non-doped device includes the following steps: ultrasonically cleaning ITO glass twice successively using acetone, alkaline detergent, ultrapure water and isopropyl alcohol for 15 minutes each time, and then processing with an ozone cleaner for 15 minutes; spin coating of a 40-nm-thick PEDOT:PSS solution on a glass base, drying in a vacuum oven at 120° C. for 45 minutes, then coating a 40-nm-thick o-dichlorobenzene solution of the compound (at a concentration of 12 mg/mL) as a light emitting layer; transferring a substrate to a vacuum chamber for thermal vapor deposition coating, and preparing an electron transport layer (TmPyPb, 50 nm), an electron injection layer (LiF, 0.5-nm) and a cathode (Al, 100 nm) to form a complete device.

Preparation of a doped device includes the following steps: respectively preparing an o-dichlorobenzene solution of a host light emitting material and an o-dichlorobenzene solution of a guest light emitting material (at a concentration of 12 mg/mL), adding 50 ul (5%) of the guest material solution with a pipette to the host material solution, and coating a light emitting layer after full magnetic stirring. Other steps are the same as the specific steps of preparation of the non-doped device.

In one embodiment, the solution processing method is an ink-jet printing method.

The organic light emitting display device according to the present disclosure may be, e.g., a mobile phone screen, a computer screen, an LCD TV screen, or the like.

In order to develop an OLED material for ink-jet printing, the present disclosure presents a star-shaped structure design, i.e., forming a six-armed and highly ordered isotropic molecule having a homogenous three-dimensional structure using a triphenylamine group having a star-shaped structure, by binding 3 $sp^3$ C atoms to truxenone (core), and using the alkyl chain for hydrotropy, so as to not only keep specific advantages of small molecule structures, but also achieve good solubility and wettability of dendrimers, and further facilitate film formation by solution processing.

The compound expressed by formula (I) of the present disclosure has thermally activated delayed fluorescence (TADF) properties, and can emit light using triplet excitons of traditional forbidden transition in fluorescent molecules to improve the device efficiency. The root cause is that HOMO and LUMO are respectively arranged on different units of the compound expressed by formula (I), and achieve complete separation, so the compound has a low $\Delta E_{ST}$ and meets reverse intersystem crossing (RISC) of energy from a triplet state to a singlet state, thereby improving the radiant efficiency.

Because of its bipolarity, the TADF material, if used as a light emitting layer, will be greatly improve injection and transmission of two types of carriers, thus reducing the device voltage. Furthermore, the light emitting layer of the device is free from a precious metal, and material waste can be avoided by means of solution processing, so that the cost can be greatly reduced.

DETAILED DESCRIPTION OF THE EMBODIMENTS

Figure 1A:
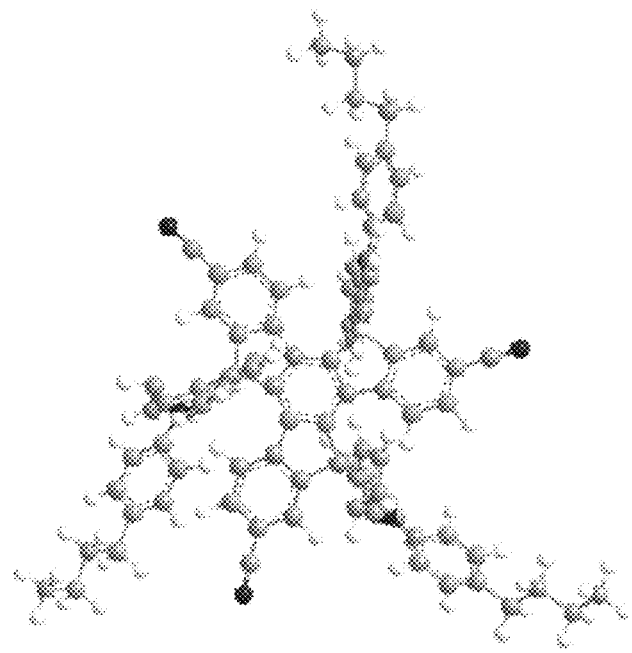
FIG. 1A is a front view of the 3D ball-and-stick model of a compound M1.

While the present disclosure will be further described in conjunction with the embodiments below, it may be understood that the embodiments are only provided for description of the present disclosure, but do not limit the contents of the present disclosure.

In one aspect according to the present disclosure, there is provided a compound having a structure expressed by formula (I),

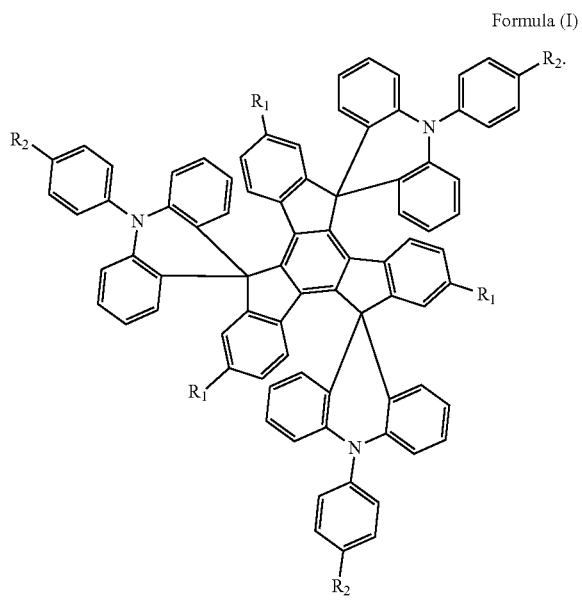

Formula (I)

Where $R_1$ is any one selected from halogen, —$CF_3$, —$NO_2$, —CN, phenyl, biphenyl, naphthyl, fluorenyl, triazinyl, triazolyl, tetrazolyl, benzimidazolyl, benzoxazolyl, dibenzothiophene sulfonyl, dibenzothiophenyl, pyridyl, pyrimidyl, quinolyl, isoquinolyl, substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl; $R_2$ is any one selected from a C1 to C20 linear or branched alkyl group and a C1 to C20 linear or branched alkoxy group; in one embodiment, $R_2$ is any one selected from a C1 to C8 linear or branched alkyl group and a C1 to C8 linear or branched alkoxy group; and in another embodiment, $R_2$ is any one selected from the group consisting of methyl, ethyl, propyl, isopropyl, butyl, isobutyl, sec-butyl, tert-butyl, —$(CH_2CH_3)CH_2CH_2CH_2CH_2CH_3$, methoxy, ethoxy, propoxy, isopropoxy, butoxy, isobutoxy, sec-butoxy and tert-butoxy; and substituent groups among the substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl, may be electron withdrawing groups, selected from more than one of halogen, —$CF_3$, —$NO_2$, and —CN.

In the technical solution of the present disclosure, the wording "substituent groups can be selected from" mean, e.g., that a substituent of substituted pyridyl may be halogen, —$CF_3$, —$NO_2$, —CN, or the like, a substituent of substituted quinolyl may also be halogen, —$CF_3$, —$NO_2$, —CN, or the like, and a substituent substituting a phenyl may be halogen, —$CF_3$, —$NO_2$, —CN, or the like.

The substitution involved above may be mono-substituted, and may also be bis-substituted or polysubstituted. In case of bis-substituted or polysubstituted, the respective substituents may be identical, totally different or partially identical.

In the technical solution of the present disclosure, the functional group (phenyl, biphenyl, naphthyl, anthryl, phenanthryl, cyclopenta[def]phenanthryl, fluorenyl, spirofluorenyl, pyrenyl, triphenylene group, fluoranthenyl, indenofluorenyl, benzofluorenyl, indenanthracenyl, dibenzofluorenyl, naphthanthracenyl, benzanthracenyl, triazinyl, triazolyl, benzimidazolyl, carbazolyl, pyridyl, pyrimidyl, quinolyl, isoquinolyl, benzothiazolyl, benzoxazolyl, dibenzothiophenyl, dibenzothiophene sulfonyl, dibenzofuryl, phenoxazinyl, phenothiazinyl) may be bound to the core of truxenone at any site, and a substituent group on the functional group can also be bound to any site of the functional group at any site, as long as the compound obtained from the binding method can be prepared.

In some embodiments, $R_1$ is any one selected from the group consisting of:

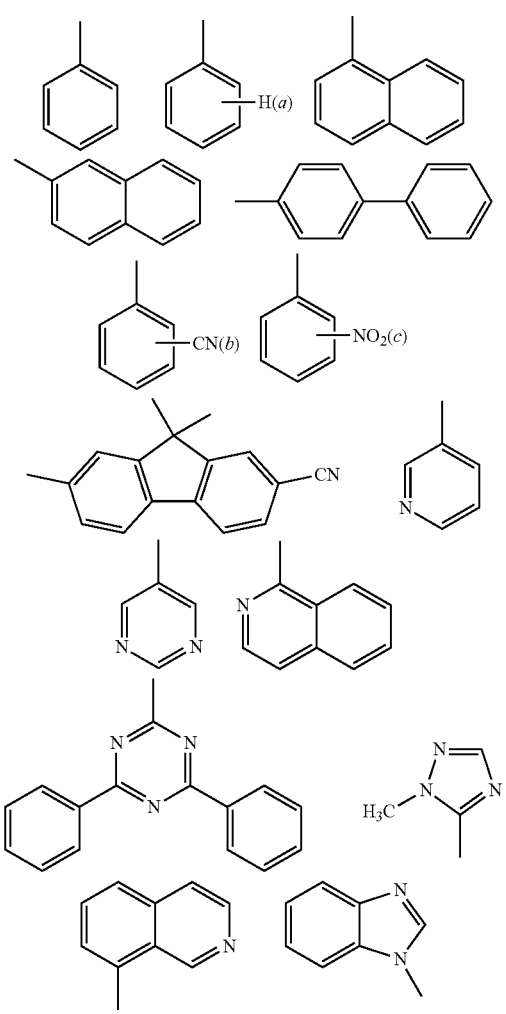
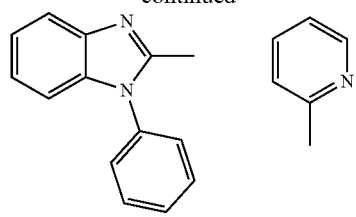
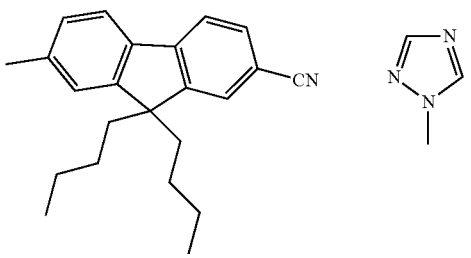
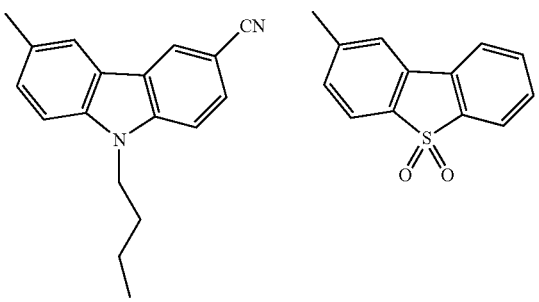
and —CN, in which a, b and c are respectively an integer independently selected from 1 to 5.
In some embodiments, the phenylindeny compounds according to the present disclosure are selected from compound M1 to compound M24 as follows:
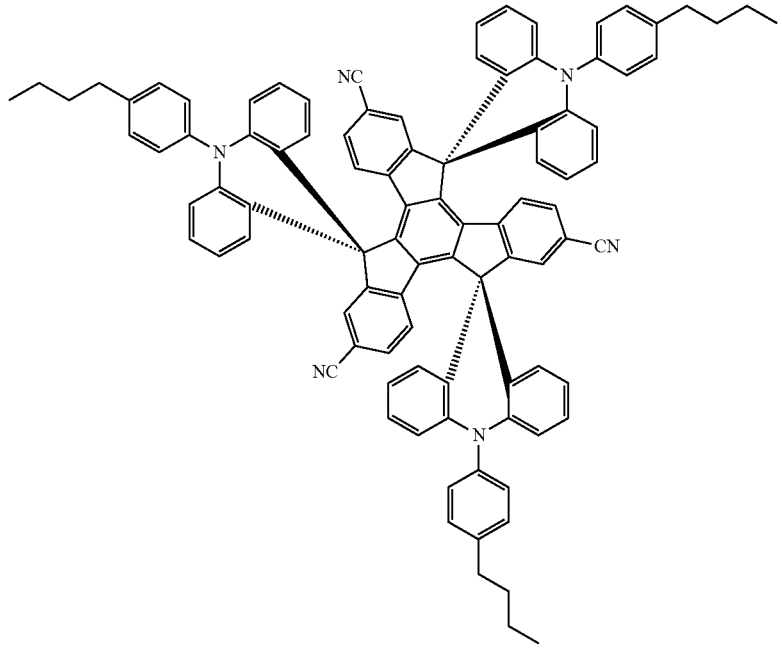
M1

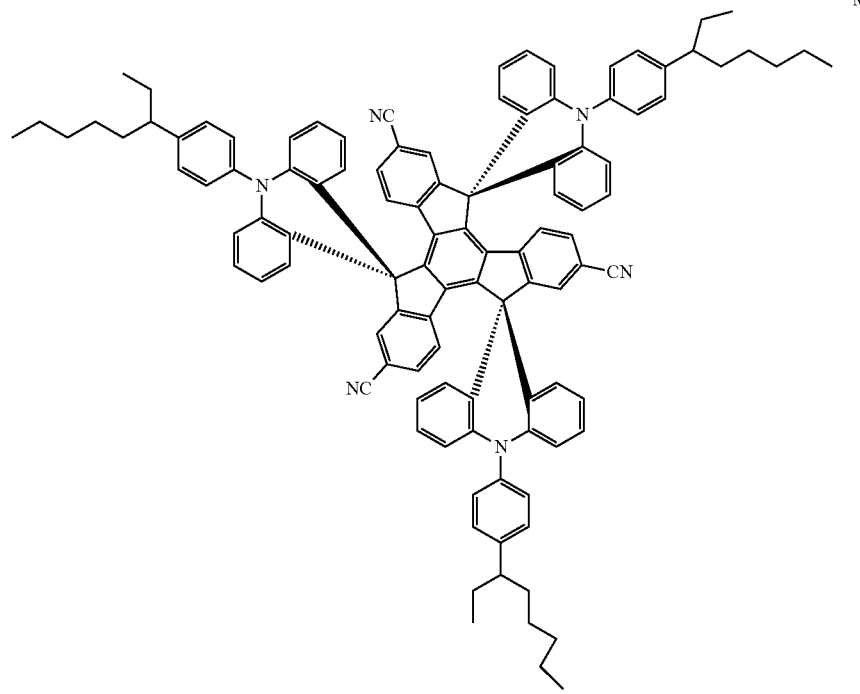
M2
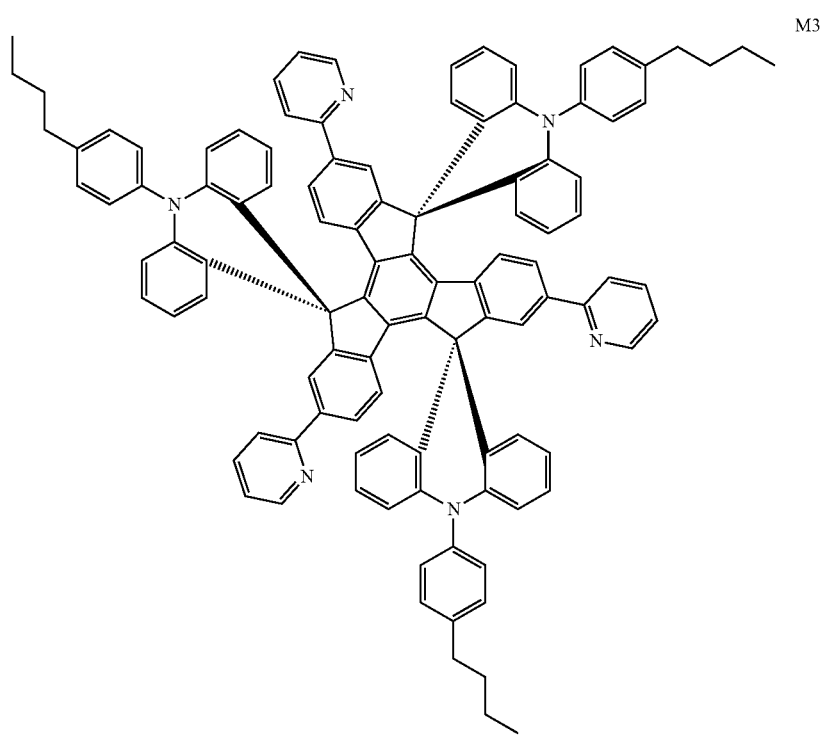
M3

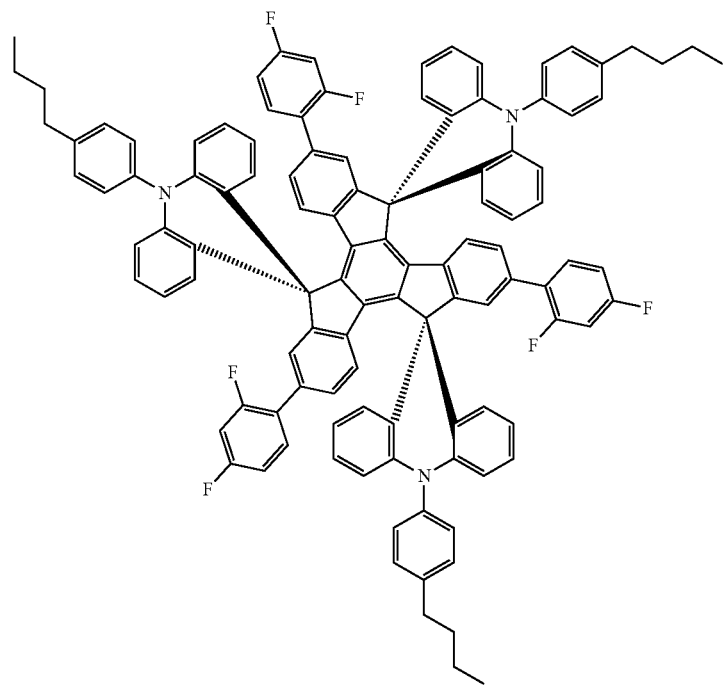
M4
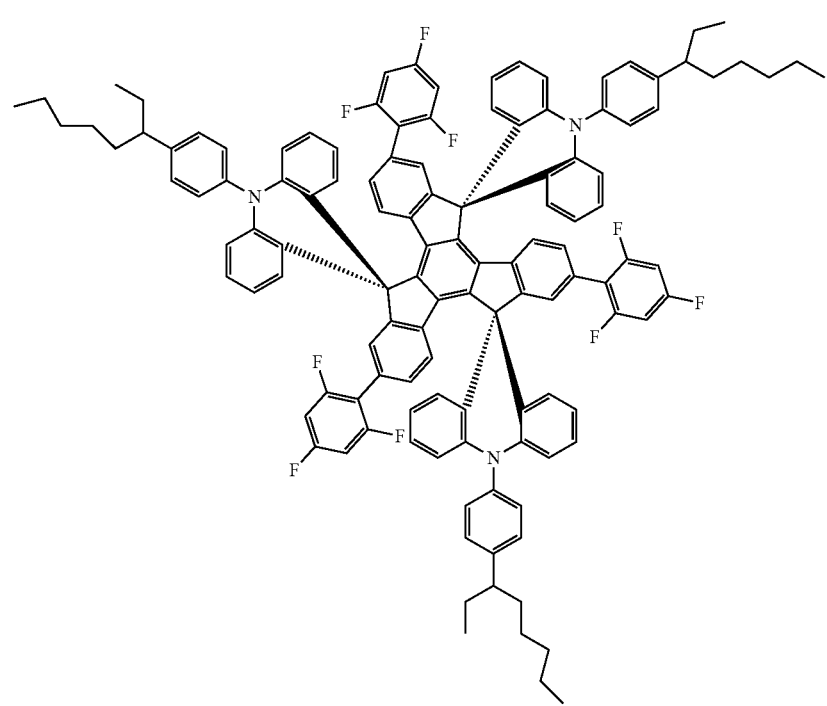
M5

M6
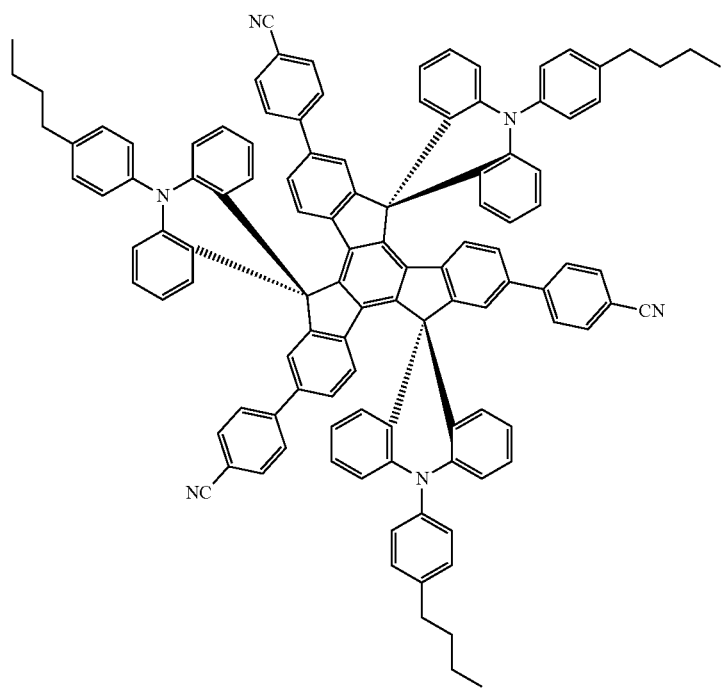
M7
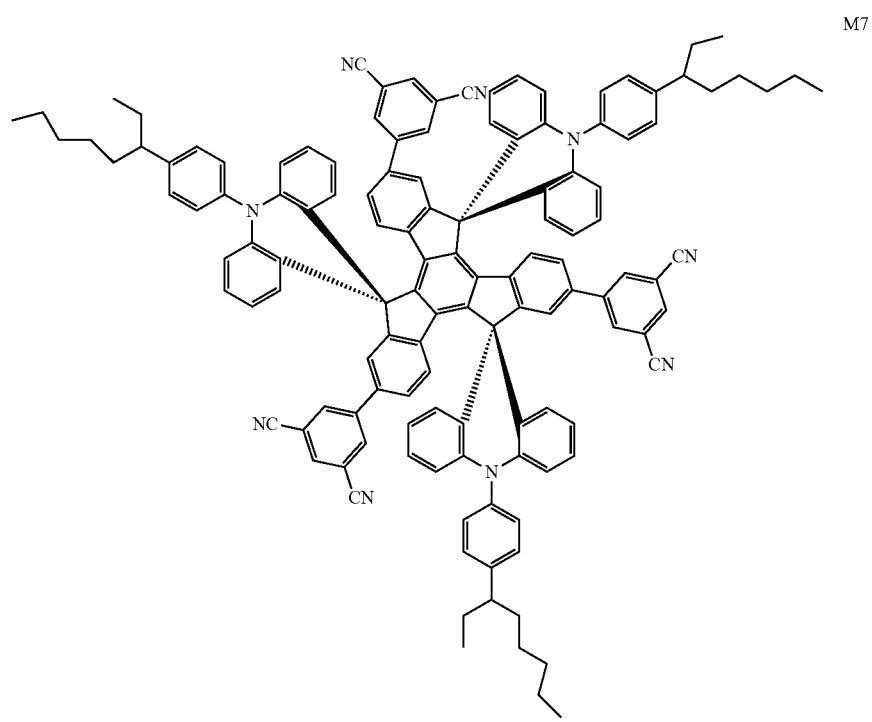

-continued
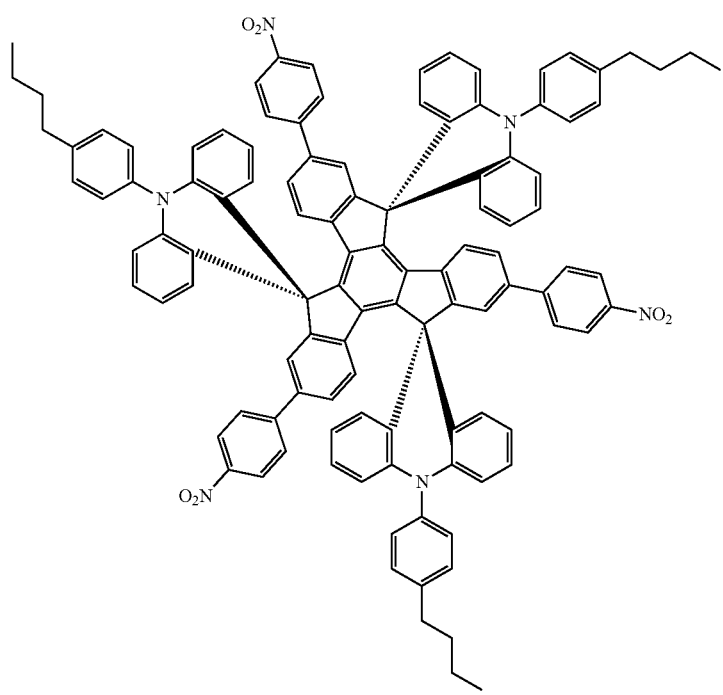
M8
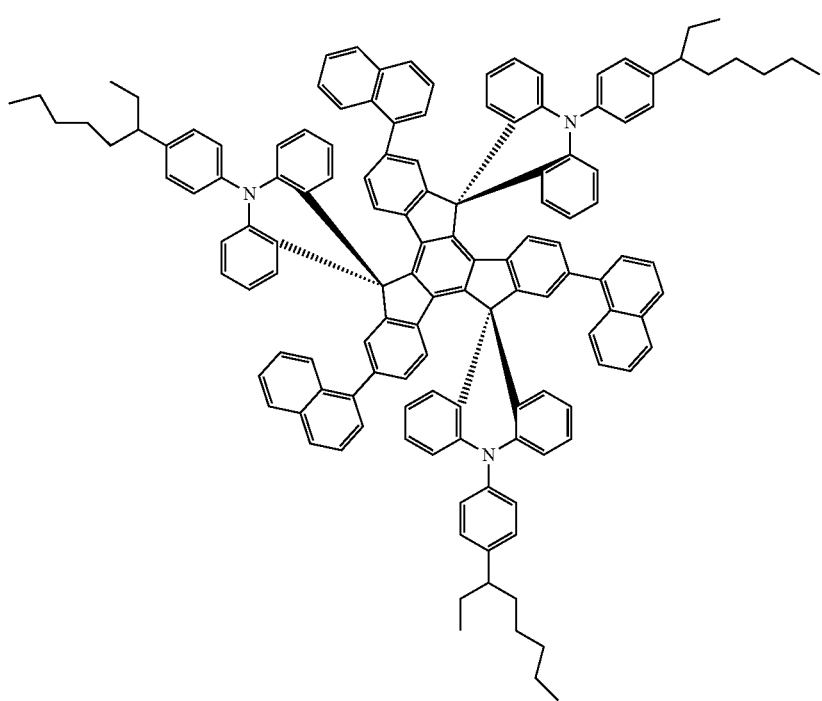
M9

M10
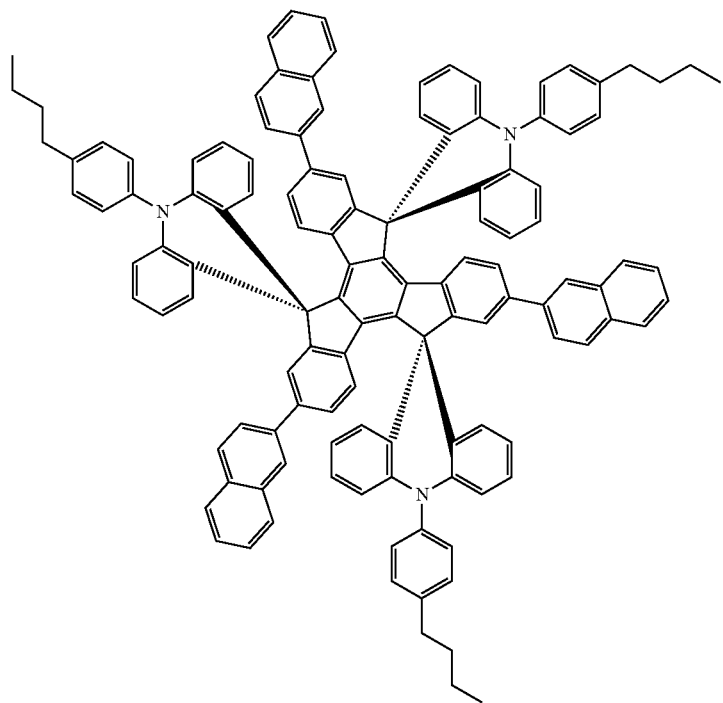
M11
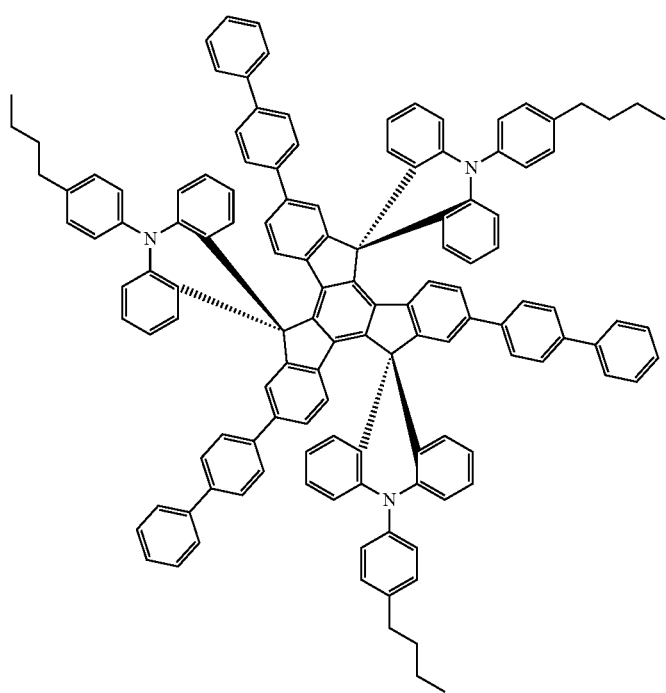

-continued
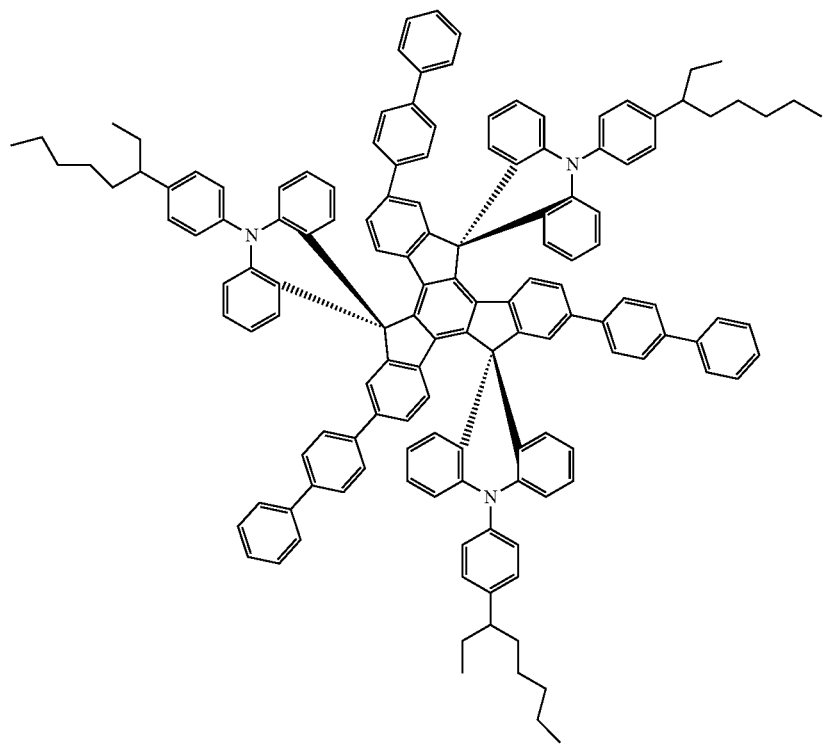
M12
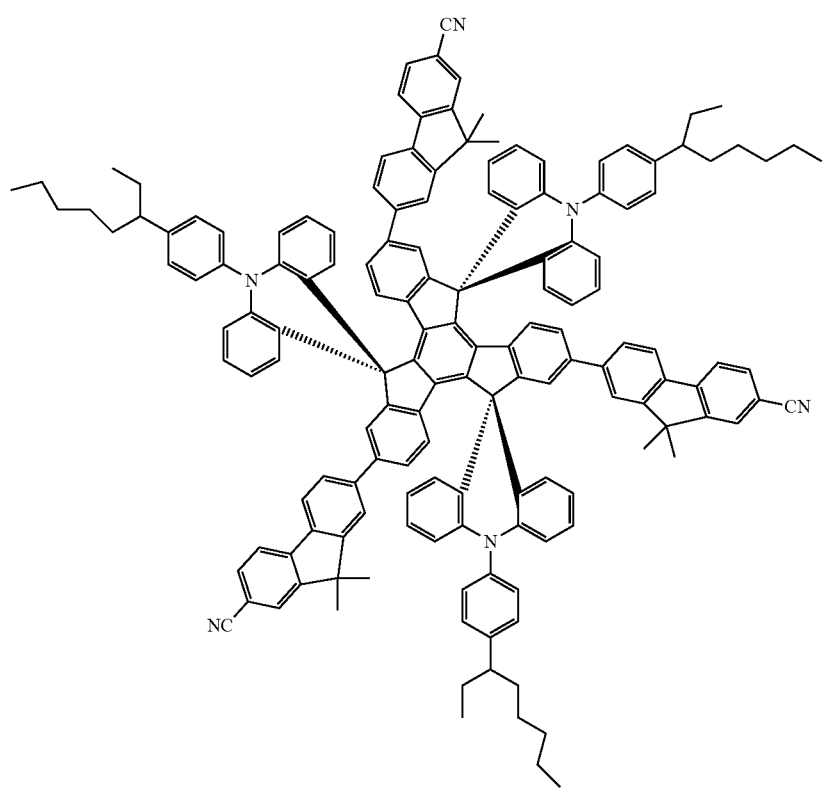
M13

M14
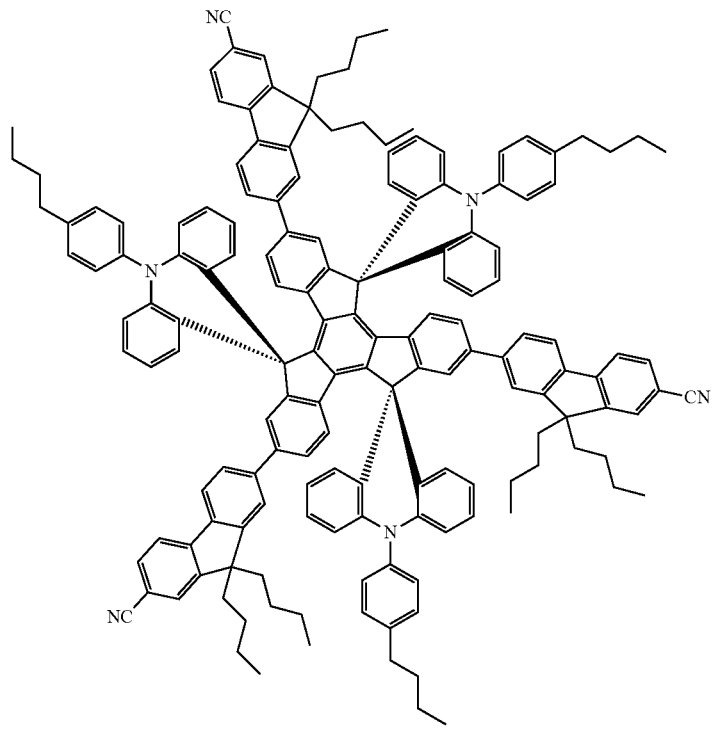
M15
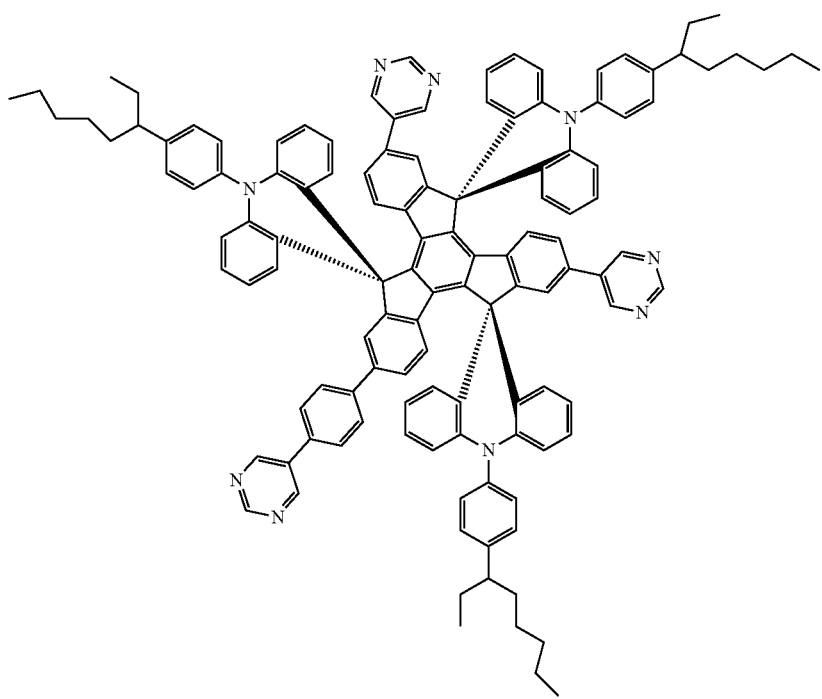

M16
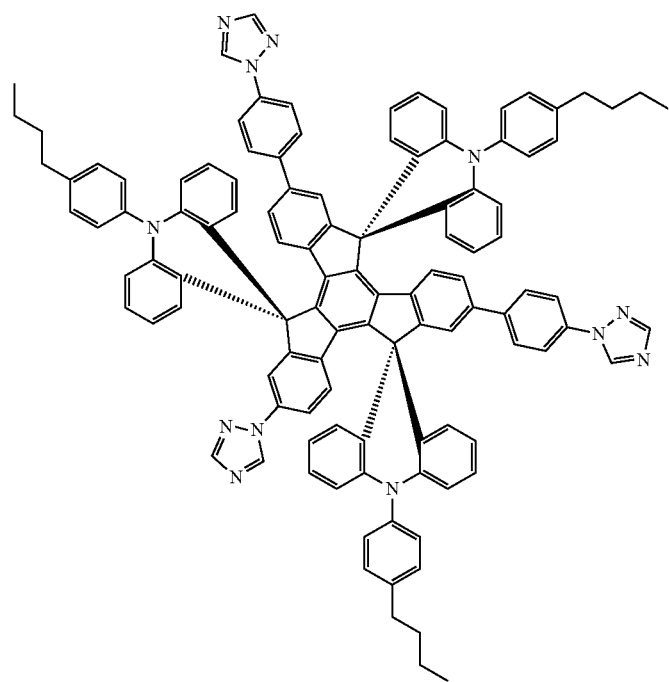
M17
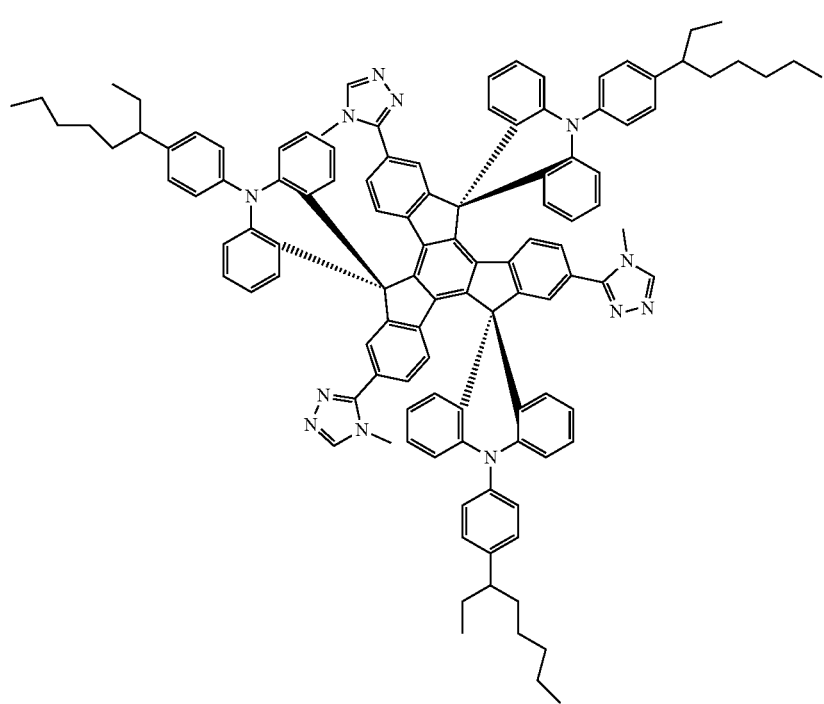

M18
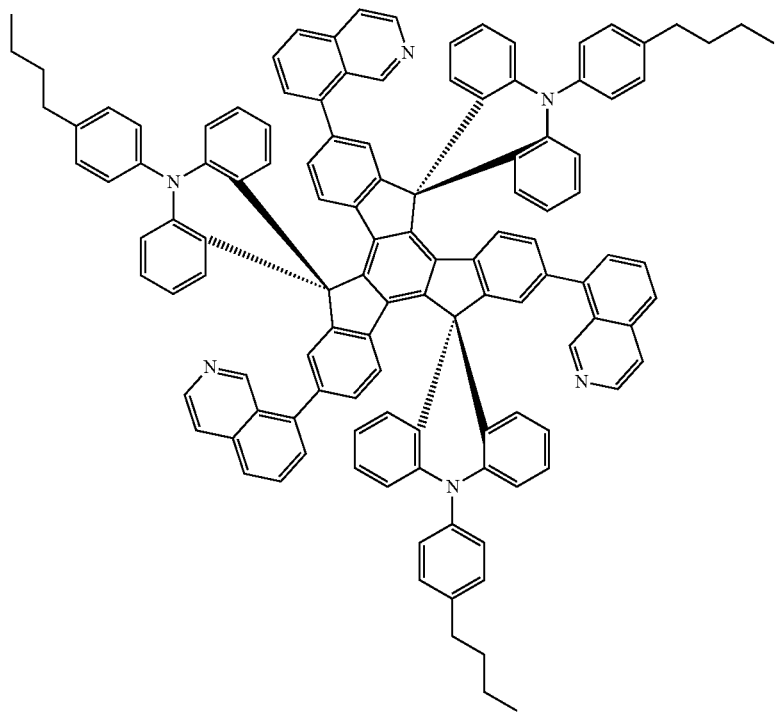
M19
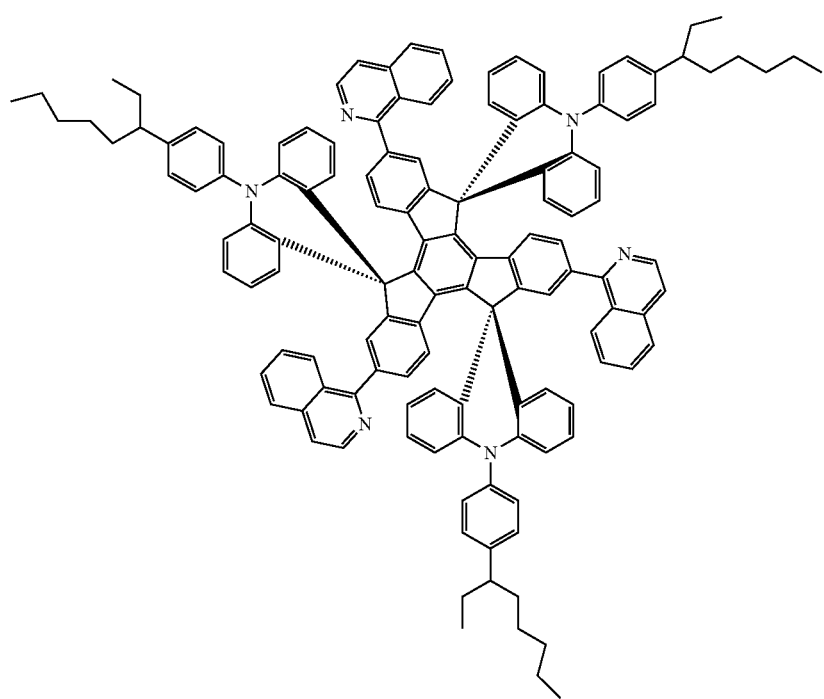

M20
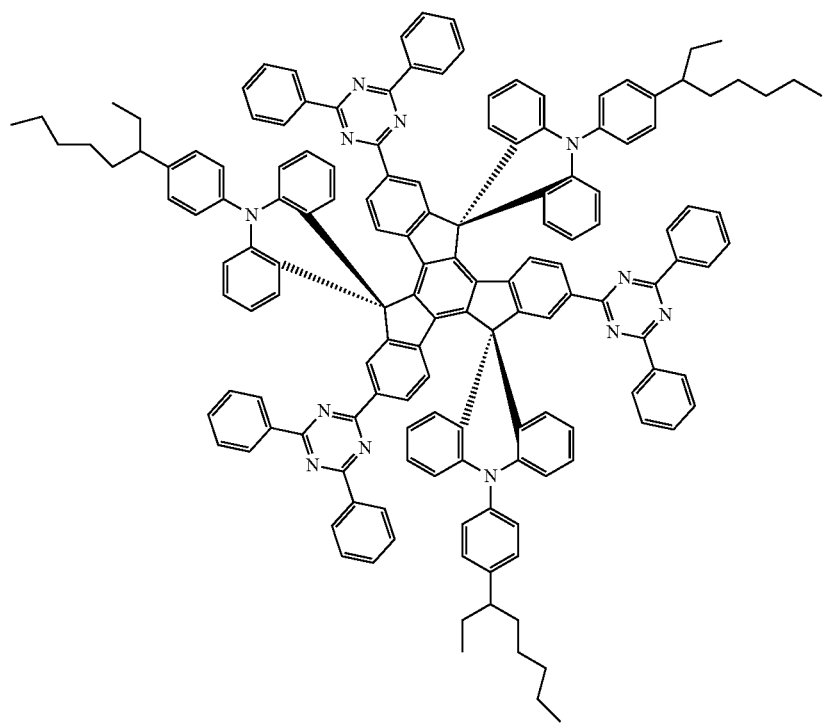
M21
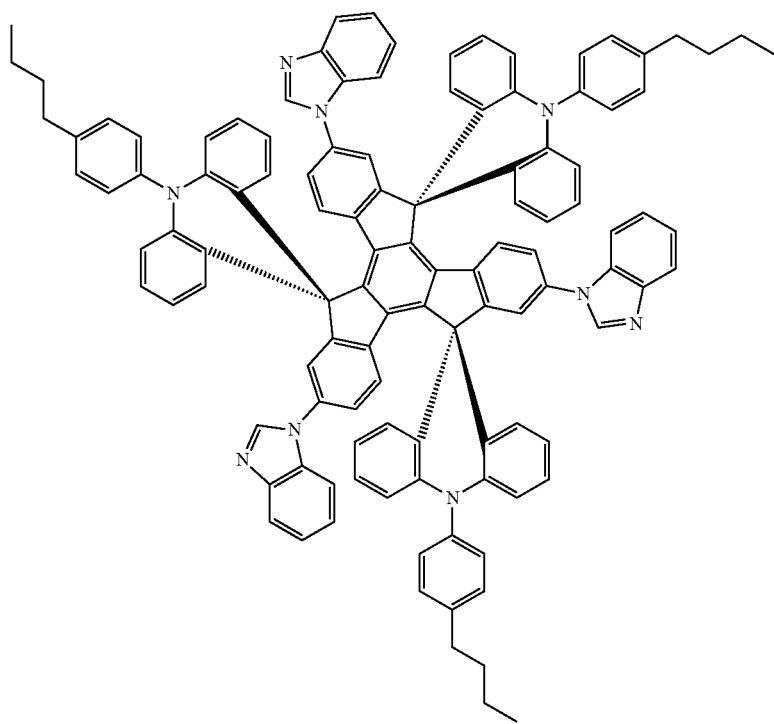

-continued
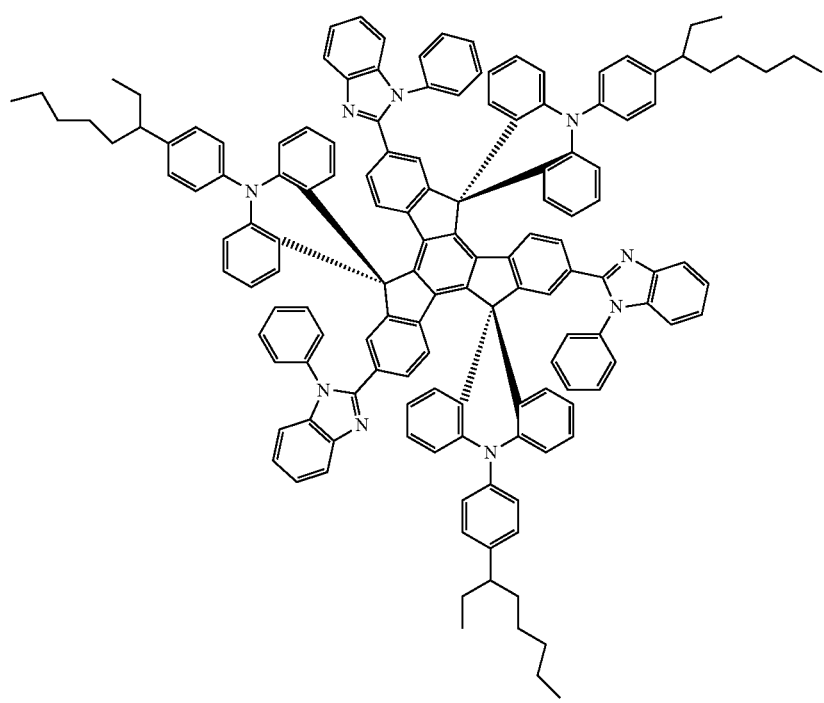
M22
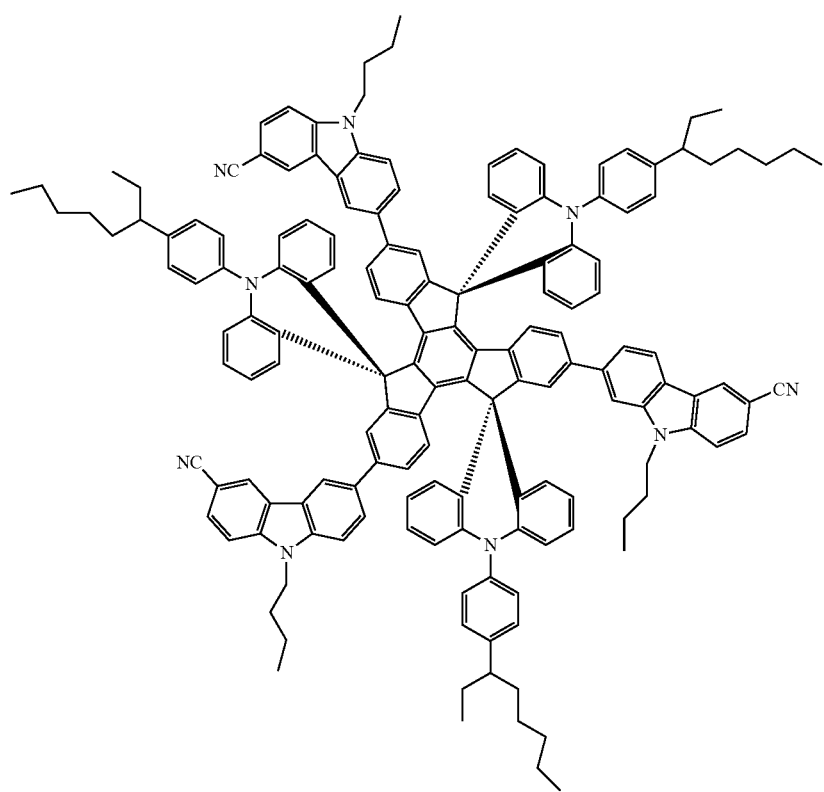
M23

M24

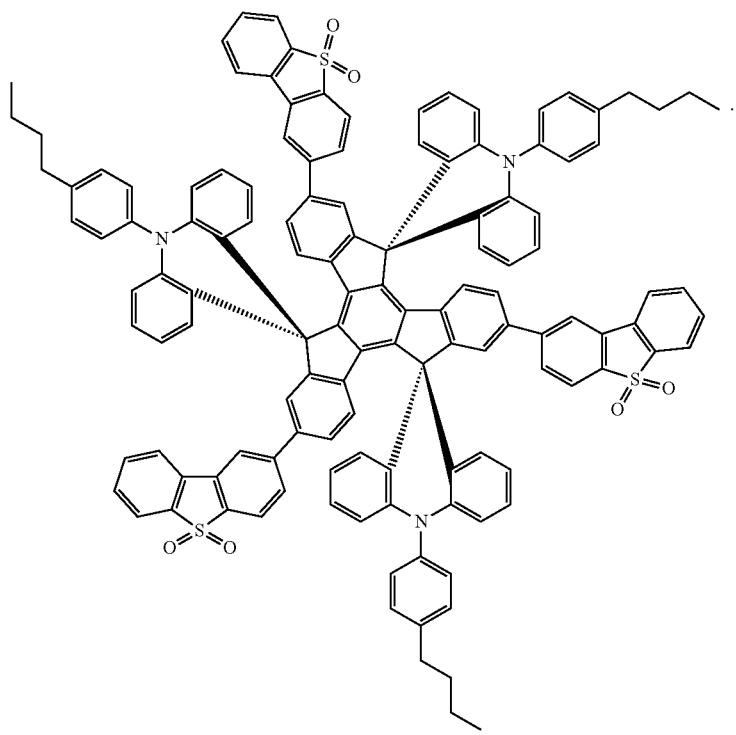

In some embodiments the compound is expressed by formula (II),

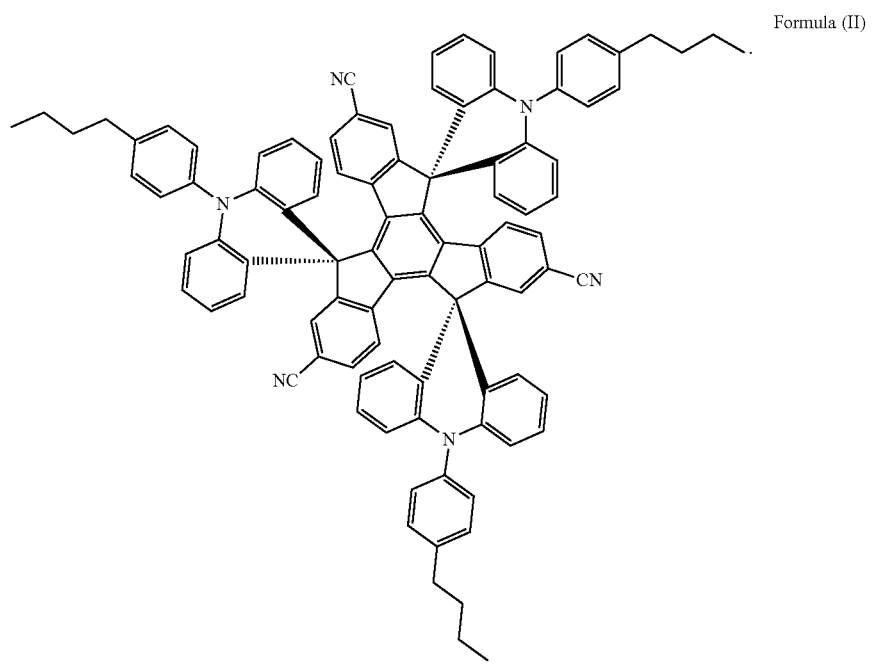 [SMILES: CCCCc1ccc(N2c3ccccc3[C@]3(c4cc(C#N)ccc4-c4c3c3c(c5c4[C@]4(c6cc(C#N)ccc6-5)c5ccccc5N(c5ccc(CCCC)cc5)c5ccccc54)[C@]4(c5cc(C#N)ccc5-3)c3ccccc3N(c3ccc(CCCC)cc3)c3ccccc34)c3ccccc32)cc1]

Formula (II)

In another aspect according to the present disclosure, there is provided a preparation method of the compound as mentioned above, including the following steps.

(1) preparing truxenone using a raw material of 1,3-indandione, and obtaining a compound expressed by formula (III) through a substitution reaction,

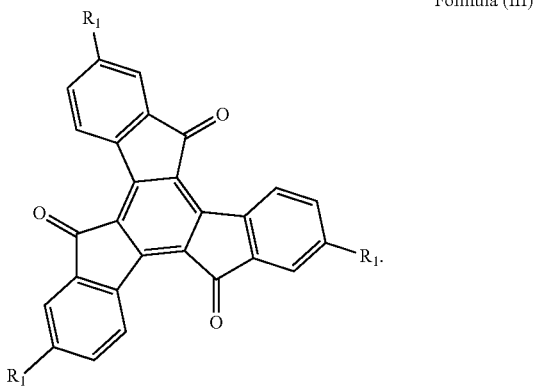

Formula (III)

(2) obtaining a compound expressed by formula (I) through a condensation reaction of the compound expressed by formula (III) and a compound expressed by formula (IV),

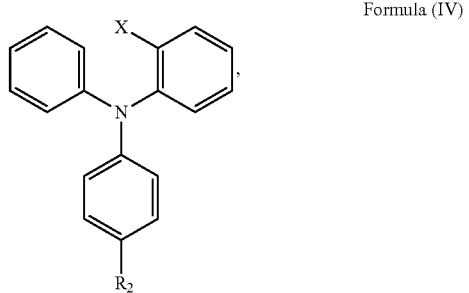

Formula (IV)

X is any one selected from halogen, for example, bromine.

It should be noted that the same reference letter refers to identical substituent throughout formula (I) of the present disclosure, i.e., three $R_1$s in formula (I) refer to three substituents identical to each other, and three $R_2$s refer to three substituents identical to each other. Like reference letters in formulae (I) and (IV) of the present disclosure may also be understood in the same way.

According to the preparation method of the compound in the present disclosure, the target product can be obtained through substitution and condensation of the simplest raw of material 1, 3-indandione, and the route thereof is simple, environmentally friendly and cheap.

In order to describe the compound of the present disclosure in more detail, the present disclosure will be further described in conjunction with the synthetic method of the above specific compounds below.

Synthesis of a Compound M1

Figure 2:
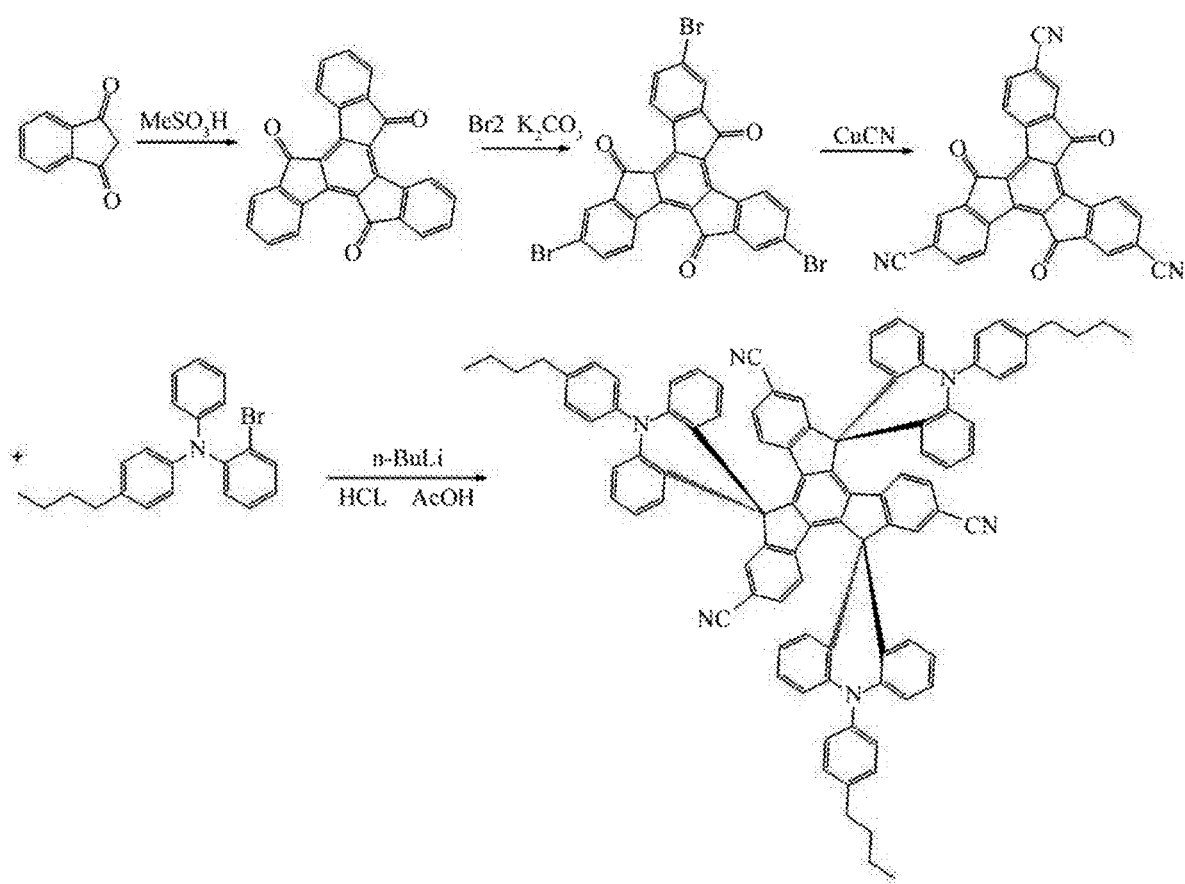
FIG. 2 is a route diagram for synthesizing a compound M1.

The route diagram for synthesizing a compound M1 is as shown in FIG. 2.

(1) Synthesis of Truxenone.

2.9 g (20 mmol) of a compound 1,3-indandione and 40 ml of methanesulfonic acid were added to a two-necked flask, heated to 110° C. and stirred for 6 h. On completion of the reaction, the solution was cooled to room temperature, and poured into ice water for quenching. A solid was separated out, was washed successively with 20 ml of a saturated sodium bicarbonate solution and 20 ml of acetone after suction filtration, and was then recrystallized with toluene to obtain 1.62 g of truxenone, which was a yellowish solid, and its yield was 63%. HRMS (ESI): m/z: 384.35. $^1$H NMR (400 MHz, CDCl$_3$): δ/ppm, 9.31 (d, 3H), 7.72 (t, 3H), 7.58 (t, 3H), 7.87 (d, 3H).

(2) Synthesis of a Compound Expressed by Formula (III).

3.8 g (9.9 mmol) of truxenone was dissolved in 50 mL of dichloromethane, 4.1 g (30 mmol) of potassium carbonate was added, and 2 mL of bromine was slowly added dropwise under a nitrogen atmosphere. The solution thus obtained was stirred at normal temperature for 24 h. On completion of the reaction, 50 mL of a saturated sodium sulfite solution was slowly added to remove unreacted bromine. After liquid was separated, the organic layer was dried and concentrated to obtain a yellowish crude product. The crude product was recrystallized with methanol to obtain 5.5 g of a brominated product, which was a white solid, and its yield was 89%.

3 g (4.8 mmol) of the brominated product and 2.3 g (25.6 mmol) of cuprous cyanide were added to 50 mL of DMF, and was stirred and refluxed for 24 h. On completion of the reaction, the reaction solution was cooled to room temperature, poured into 100 ml of a ferric chloride-hydrochloric acid solution (15 g of ferric chloride mixed with 9 ml of hydrochloric acid in 100 ml of water), then heated to 60° C., stirred for 30 min, and re-cooled to room temperature. The organic phase was extracted with dichloromethane (100 ml*3), and the concentrated product was dried and separated using column chromatography isolation (dichloromethane/petroleum ether=1/1) to obtain 0.8 g of a white solid, the yield of which was 35%. HRMS (ESI): m/z: 459.17. $^1$H NMR (400 MHz, CDCl$_3$): δ/ppm, 8.69 (s, 3H), 8.34 (d, 3H), 8.01 (d, 3H).

(3) Synthesis of a Target Compound M1.

Under a nitrogen atmosphere, 1.3 g (3.5 mmol) of 2-bromo-N-(4-butyl)triphenylamine was dissolved in 30 mL of anhydrous tetrahydrofuran solution while stirring, 2.5 mL (4.0 mmol) of 1.6Mn-BuLi was slowly added dropwise at −78° C. for 1 h, then a solution obtained by dissolving 0.45 g (0.98 mmol) of tricyanotruxenone in 5 mL of tetrahydrofuran was slowly added dropwise, naturally warmed up to room temperature, and kept overnight. On completion the reaction, the reaction was quenched with 100 mL of water, and an organic phase was obtained through extraction with dichloromethane (30 mL*3). A crude alcohol intermediate was obtained through drying, rotary evaporation for removing the solvent, washing with 10 mL of toluene, and suction filtration, was added to a mixed solution of 5 ml of concentrated HCl and 50 ml of AcOH, refluxed for 2 h, cooled to room temperature, regulated with a saturated NaHCO$_3$ solution to neutral after adding 100 ml of water, and extracted with dichloromethane (30 ml*3) to obtain an organic phase. The solvent was removed by rotary evaporation, and then the product was purified with a column chromatography method (mobile phase n-hexane:dichloromethane=3:1) to obtain 0.48 g of a target product, which was a white solid, and its yield was 37%. MALDI-TOF: m/z: 1308.63; $^1$H NMR (CDCl$_3$, 400 MHz): δ=8.19 (d, 3H), 7.84 (s, 3H), 7.67 (d, 3H), 6.96-7.04 (m, 18H), 6.69 (t, 6H), 6.51-6.58 (m, 12H), 2.62 (t, 6H), 1.59 (m, 6H), 1.31 (m, 6H), 0.90 (t, 9H).

Compounds M1 to M24 were synthesized using a method similar to the method for synthesizing the compound M1.

In another aspect, the present disclosure provides an organic light emitting display device, including an organic electroluminescent device which includes: an organic functional layer, comprising one or more organic film layers, and at least one of the organic film layers is a light emitting layer; and the light emitting layer includes a light emitting material including the compound as mentioned above.

The organic electroluminescent device further comprises: a base; a first electrode arranged on the base; and a second electrode arranged on the organic functional layer, and the organic functional layer is arranged on the first electrode.

In some embodiments, the light emitting material is a blue thermally activated delayed fluorescence material.

In some embodiments, the light emitting material is a host material or a guest material of the light emitting layer. When the light emitting material is used as the host material of the light emitting layer, the guest material is selected from the group consisting of BczVBi, coumarin-6, DCJTB, and the like; and when the light emitting material is used as the guest material of the light emitting layer, the host material is selected from polyvinyl carbazole (PVK) and polyfluorene (PFO).

The organic functional layer according to the present disclosure further includes a hole injection layer, a hole transport layer, an electron transport layer and an electron injection layer.

Figure 6:
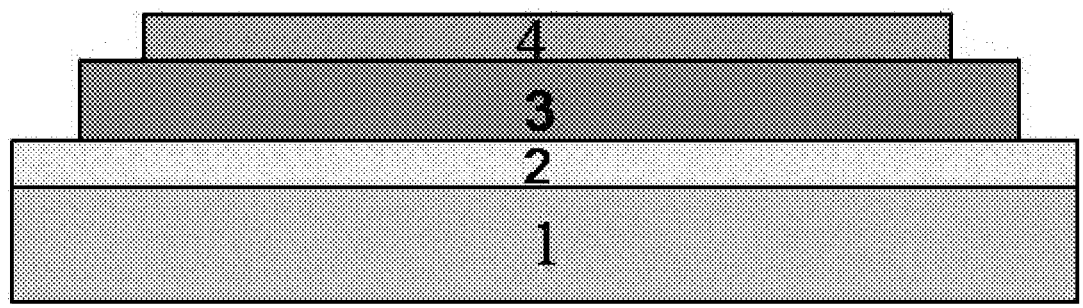
FIG. 6 is a structure diagram of an organic electroluminescent device according to the present disclosure.

According to the present disclosure, a structure of the organic electroluminescent device is shown in FIG. 6, and a base 1 is made from glass or other suitable materials (e.g. plastic); a first electrode 2 is a transparent electrode, such as ITO or IGZO; an organic functional layer 3 includes one or a more organic film layers; and a second electrode 4 is a metallic cathode, and the first electrode 2 and the second electrode 4 are interchangeable, i.e. the first electrode 2 is a metallic cathode, and the second electrode 4 is a transparent electrode, such as ITO or IGZO.

In some embodiments, the organic electroluminescent device is manufactured using a solution processing method.

Preparation of a non-doped device includes the following steps: ultrasonically cleaning ITO glass twice successively using acetone, alkaline detergent, ultrapure water and isopropyl alcohol for 15 minutes each time, and then processing with an ozone cleaner for 15 minutes; spin coating of a 40-nm-thick PEDOT:PSS solution on a glass base, drying in a vacuum oven at 120° C. for 45 minutes, then coating a 40-nm-thick o-dichlorobenzene solution of the compound (at a concentration of 12 mg/mL) as a light emitting layer; transferring a substrate to a vacuum chamber for thermal vapor deposition coating, and preparing an electron transport layer (TmPyPb, 50 nm), an electron injection layer (LiF, 0.5-1 nm) and a cathode (Al, 100 nm) to form a complete device.

Preparation of a doped device includes the following steps: respectively preparing an o-dichlorobenzene solution of a host light emitting material and an o-dichlorobenzene solution of a guest light emitting material (at a concentration of 12 mg/mL), adding 50 ul (5%) of the guest material solution with a pipette to the host material solution, and coating a light emitting layer after full magnetic stirring. Other steps are the same as the specific steps of preparation of the non-doped device.

In some embodiments, the solution processing method is an ink-jet printing method.

Figure 7:
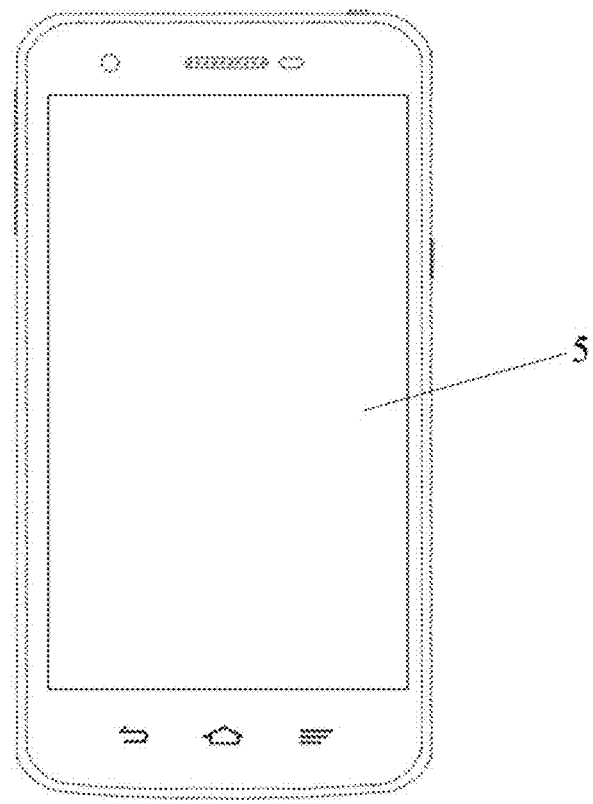
FIG. 7 is a schematic diagram of a mobile phone screen.

The organic light emitting display device according to the present disclosure may be, e.g., a mobile phone screen, a computer screen, an LCD TV screen, or the like, which is not specially limited in this example. FIG. 7 is a schematic diagram of a mobile phone screen, and 5 represents a display screen.

Thus it can be seen that there are many optional factors for the compounds and the organic light emitting display devices according to the present disclosure, which can be combined into different embodiments according to the claims of the present disclosure. The embodiments of the present disclosure are only used as specific description of the present disclosure, but are not used to limit the present disclosure. The present disclosure will be further described in conjunction with the embodiments of the organic electroluminescent device containing the compounds of the present disclosure below.

Embodiments 1 to 8

Figure 1B:
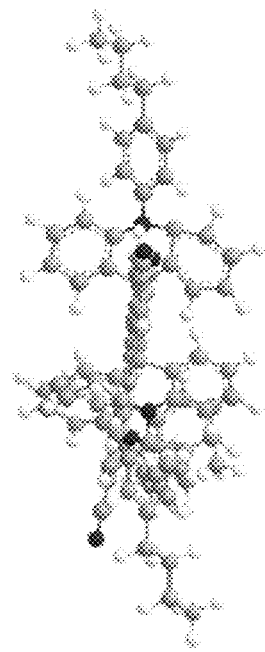
FIG. 1B is a side view of the 3D ball-and-stick model of a compound M1.

FIG. 1A is a front view of the 3D ball-and-stick model, and FIG. 1B is a side view of the 3D ball-and-stick model. It can be seen that the triphenylamine (donor) is practically perpendicular to the cyanotruxenone (acceptor). This highly twisted structure helps to reduce $\Delta E_{ST}$ and improve the reverse intersystem crossing ability, thereby enhancing the luminous efficiency.

Figure 3A:
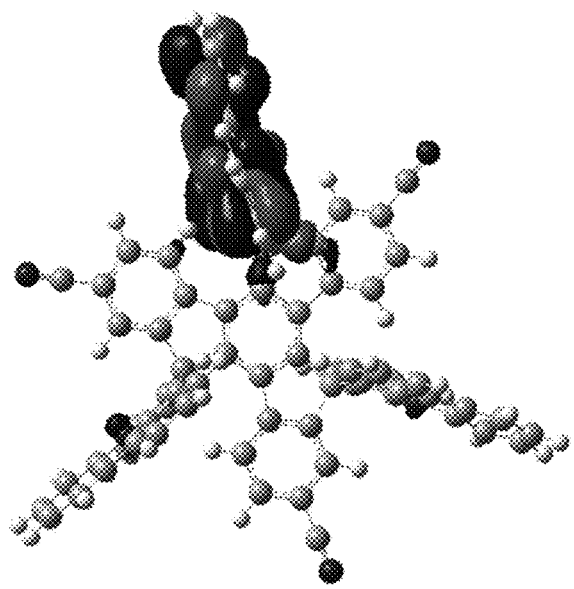
FIG. 3A is an energy level distribution diagram of HOMO of the compound M1.
Figure 3B:
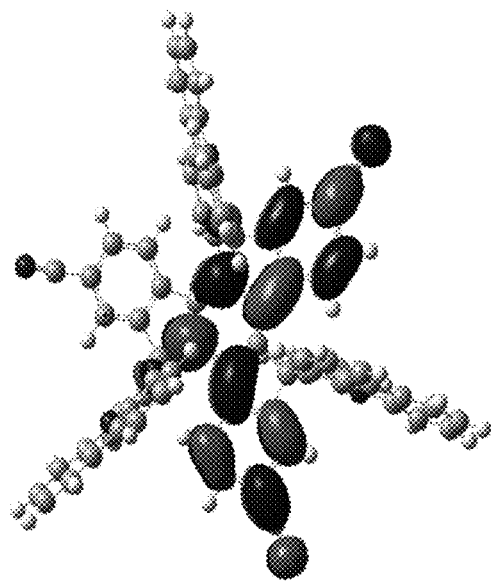
FIG. 3B is an energy level distribution diagram of LUMO of the compound M1.

FIG. 3A is an energy level distribution diagram of HOMO of the compound M1, and FIG. 3B is an energy level distribution diagram of LUMO of the compound M1. As can be obviously seen from FIG. 3A and FIG. 3B, HOMO and LUMO of M1 molecules are respectively arranged on different units, and achieve complete separation, thereby facilitating reducing the intersystem energy difference $\Delta E_{ST}$, and improving the reverse intersystem crossing ability.

The molecular frontier orbital distribution of compounds M1 to M4, M9, M17, M20 and M24 was optimized and calculated using the density functional theory (DFT) at a calculation level of B3LYP/6-31G(d) using a Gaussian 09 software package. Furthermore, the fluorescence life of the compounds M1 to M4, M9, M17, M20 and M24 was calculated using Einstein spontaneous radiation formula based on the time dependent density functional theory (TDDFT).

As can be seen from relevant data of embodiments 1 to 8 shown in Table 1, the $\Delta E_{ST}$ of all compounds is less than 0.2 ev, thereby achieving smaller energy level difference between a singlet state and a triplet state. Furthermore, the fluorescence life of all compounds is in an order of magnitude of microsecond, and has an obvious delayed fluorescence effect. (In Table 1, $S_1$ represents a singlet state energy level, $T_1$ represents a triplet state energy level, $\Delta E_{ST}$ represents an energy level difference between a singlet state and a triplet state. Eg represents a HOMO-LUMO energy level difference, and r represents a fluorescence life.)

TABLE 1

| Embodiment | Compound | HOMO (ev) | LUMO (ev) | $S_1$ (ev) | $T_1$ (ev) | $\Delta E_{ST}$ (ev) | Eg (ev) | τ (μS) |
|---|---|---|---|---|---|---|---|---|
| 1 | M1  | −5.58 | −2.23 | 2.75 | 2.63 | 0.12 | 3.35 | 3.1 |
| 7 | M2  | −5.63 | −2.21 | 2.68 | 2.55 | 0.13 | 3.42 | 1.6 |
| 3 | M3  | −5.51 | −2.46 | 2.56 | 2.49 | 0.07 | 3.05 | 5.9 |
| 4 | M4  | −5.55 | −2.39 | 2.51 | 2.41 | 0.10 | 3.16 | 1.7 |
| 5 | M9  | −5.43 | −2.11 | 2.71 | 2.54 | 0.17 | 3.32 | 0.5 |
| 6 | M17 | −5.52 | −2.32 | 2.65 | 2.57 | 0.08 | 3.20 | 6.4 |
| 7 | M20 | −5.77 | −2.63 | 2.53 | 2.48 | 0.05 | 3.14 | 11.9 |
| 8 | M24 | −5.69 | −2.38 | 2.56 | 2.49 | 0.07 | 3.31 | 2.5 |

A non-doped device N1 was designed with the compound M1 as a light emitting material, and its structure is as follows: ITO (100 nm)/PEDOT:PSS (40 nm)/M1 (40 nm)/TmPyPb (50 nm)/LiF (0.5 nm)/Al (100 nm).

Doped devices N1 to N4, N9, N17, N20 and N24 were designed with the compounds M1 to M4, M9, M17, M20 and M24 as fluorescent dopants, and with a typical polymer material PVK as a host material, and their structure is as follows:
ITO (100 nm)/PEDOT:PSS (40 nm)/PVK:M (40 nm)/TmPyPb (50 nm)/LiF (0.5 nm)/Al (100 nm). Moreover, a doped device C1 as a contrast was designed with BCzVBi as a fluorescent dopant, and with a typical polymer material PVK as a host material, and its structure is as follows: ITO (100 nm)/PEDOT:PSS (40 nm)/PVK:BCzVBi (40 nm, 5%)/TmPyPb (50 nm)/LiF (0.5 nm)/Al (100 nm).

Figure 4A:
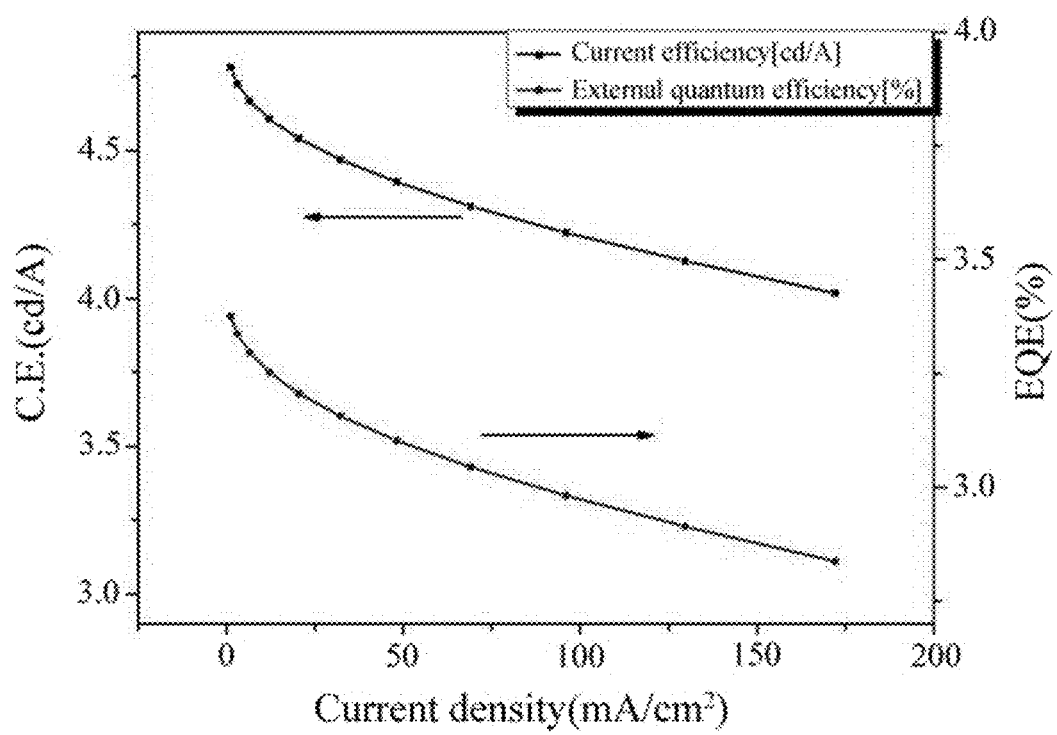
FIG. 4A is a curve graph of current efficiency and an external quantum efficiency of a device N1 (non-doped).
Figure 4B:
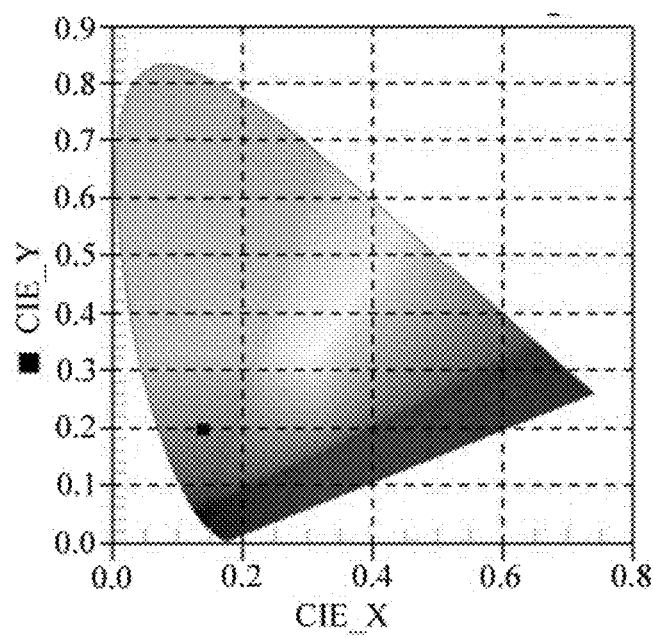
FIG. 4B is a CIE coordinate graph of the device N1 (non-doped).
Figure 5A:
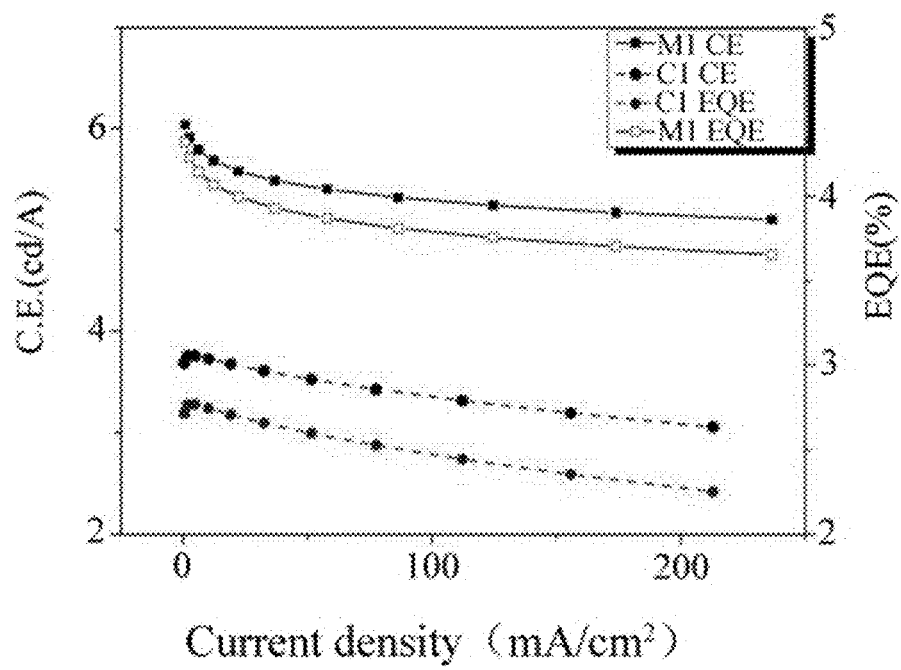
FIG. 5A is a curve graph of current efficiency and an external quantum efficiency of a device N1 (doped).
Figure 5B:
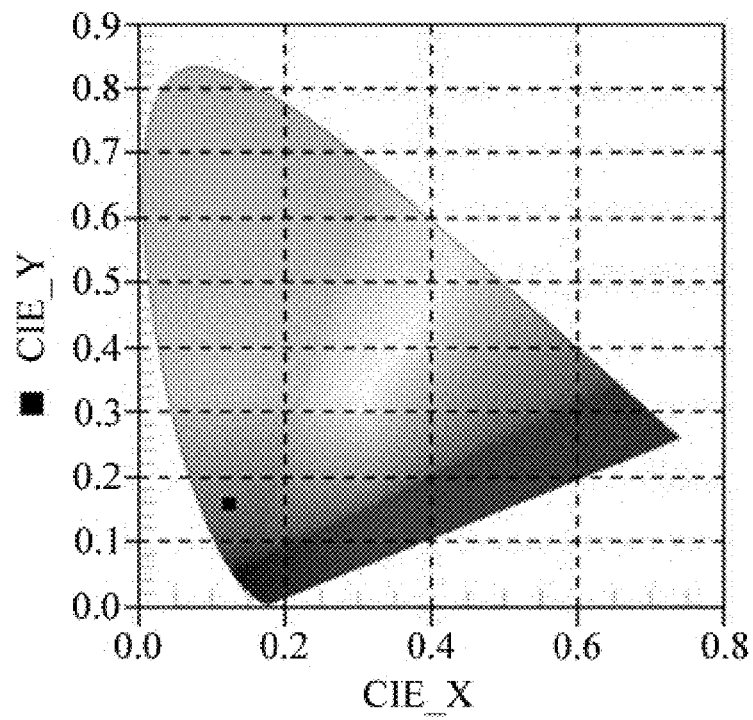
FIG. 5B is a CIE coordinate graph of light emitting of the device N1 (doped).

Relevant data of the above devices are shown in Table 2. FIGS. 4A to 4B also shows a J-V-B, an efficiency curve and CIE coordinates of a device N1 (non-doped), where FIG. 4A shows a curve graph of current efficiency and an external quantum efficiency of the device, and FIG. 4B is a CIE coordinate graph of light emitting of the device. FIGS. 5A to 5B shows a J-V-B, an efficiency curve and CIE coordinates of a device N1 (doped) and a contrast device C1, where FIG. 5A is a curve graph of current efficiency and an external quantum efficiency of the device N1 (doped), and FIG. 5B is a CIE coordinate graph of light emitting of the device N1 (doped).

As can see from Table 2 and FIGS. 4A to 4B, a non-doped device with M1 as a host light emitting material has achieved 3.40% maximum external quantum efficiency, showing that owning to the high twisting strength, highly regularity and peripherally highly branched alkyl chain of the material, the exciton quenching problem caused by π-π stacking was effectively reduced, thus obtaining satisfactory device performance.

A doped device with a classic polymer material PVK as a host, and with M1 as a light emitting guest/dopant has achieved 4.32% maximum external quantum efficiency, which is further enhanced compared with non-doped devices, showing that doping methods can better avoid π-π stacking effect.

As can be seen from Table 2 and FIGS. 5A to 5B, compared with the contrast device C1 using a classic blue light emitting BCzVBi as a fluorescent dopant, an $EQE_{(Max)}$ (%) of the N1 (doped) device is increased by about 60%. This is mainly because of the TADF properties of M1 itself, light can be emitted using triplet excitons of traditional forbidden transition in fluorescent molecules (e.g. BCzVBi), thereby improving the device efficiency. Furthermore, the two devices have equivalent CIE performance, and both emit pure blue light. N2 (doped) devices, N3 (doped) devices, N4 (doped) devices, N9 (doped) devices, N17 (doped) devices, N20 (doped) devices and N24 (doped) devices all have an $EQE_{(Max)}$(%) of above 3.75%, and emit pure blue light. (In Table 2, $V_{turn-on}$ represents a turn-on voltage, $E_{L(max)}/E_{L(10\ mA/cm^2)}$ represents a current efficiency when maximum current efficiency/current density= $10_{mA/cm^2}$, $h_{p(max)}$ represents a maximum power efficiency, $EQE_{(max)}$ represents a maximum external quantum efficiency, and $CIE_{(x,y)}$ represents color coordinates.)

TABLE 2

| Device | Doped or not | $V_{turn-on}$ [V] | $E_{L(max)}/E_{L(10\ mA/cm^2)}$ (cd A$^{-1}$) | $h_{p(max)}$ (1 m W$^{-1}$) | $EQE_{(max)}$ (%) | CIE (x, y) |
|---|---|---|---|---|---|---|
| N1  | Non-doped | 4.7 | 4.78/4.61   | 3.13 | 3.40 | (0.141, 0.195) |
| N1  | Doped     | 4.1 | 6.04/5.68   | 4.41 | 4.32 | (0.126, 0.158) |
| N2  | Doped     | 4.5 | 6.77/6.21   | 4.52 | 4.88 | (0.134, 0.141) |
| N3  | Doped     | 4.2 | 8.97/8.43   | 6.40 | 3.94 | (0.166, 0.493) |
| N4  | Doped     | 4.3 | 13.33/12.75 | 9.31 | 5.11 | (0.147, 0.587) |
| N9  | Doped     | 4.8 | 5.11/4.70   | 3.21 | 3.75 | (0.134, 0.117) |
| N17 | Doped     | 4.5 | 5.72/5.36   | 3.82 | 4.09 | (0.158, 0.212) |
| N20 | Doped     | 4.3 | 14.51/13.05 | 9.89 | 5.56 | (0.135, 0.428) |
| N24 | Doped     | 4.3 | 12.02/11.14 | 8.03 | 4.61 | (0.175, 0.380) |
| C1  | Doped     | 3.9 | 3.76/3.73   | 2.90 | 2.77 | (0.146, 0.144) |

Obviously, various modifications and variations of the present disclosure may also be made by persons skilled in the art without departing from the spirit and scope of the present disclosure. Thus, if these modifications and variations of the present disclosure fall within the scope of the claims and equivalents thereof of the present disclosure, the present disclosure is also intended to be included in these modifications and variations.

What is claimed is:
1. A compound, having a structure expressed by formula (I),

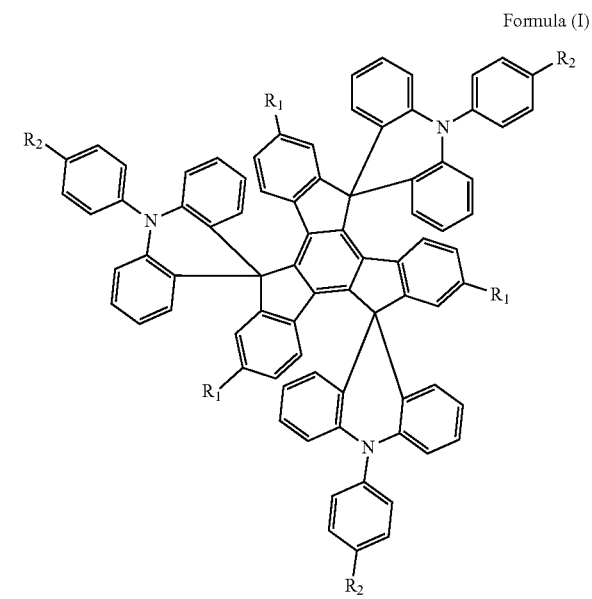

Formula (I)

wherein, $R_1$ is any one selected from halogen, —$CF_3$, —$NO_2$, —CN, phenyl, biphenyl, naphthyl, fluorenyl, triazinyl, triazolyl, tetrazolyl, benzimidazolyl, benzoxazolyl, dibenzothiophene sulfonyl, dibenzothiophenyl, pyridyl, pyrimidyl, quinolyl, isoquinolyl, substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl;

$R_2$ is any one selected from a C1 to C20 linear or branched alkyl group and a C1 to C20 linear or branched alkoxy group; and wherein substituent groups among the substituted phenyl, substituted biphenyl, substituted naphthyl, substituted anthryl, substituted phenanthryl, substituted cyclopenta[def]phenanthryl, substituted fluorenyl, substituted spirofluorenyl, substituted pyrenyl, substituted triphenylene group, substituted fluoranthenyl, substituted indenofluorenyl, substituted benzofluorenyl, substituted indenanthracenyl, substituted dibenzofluorenyl, substituted naphthanthracenyl, substituted benzanthracenyl, substituted triazinyl, substituted triazolyl, substituted benzimidazolyl, substituted carbazolyl, substituted pyridyl, substituted pyrimidyl, substituted quinolyl, substituted isoquinolyl, substituted benzothiazolyl, substituted benzoxazolyl, substituted dibenzothiophenyl, substituted dibenzothiophene sulfonyl, substituted dibenzofuryl, substituted phenoxazinyl and substituted phenothiazinyl, are selected from electron withdrawing groups.

2. The compound according to claim 1, wherein $R_2$ is any one selected from a C1 to C8 linear or branched alkyl group and a C1 to C8 linear or branched alkoxy group.

3. The compound according to claim 1, wherein $R_1$ is any one selected from the group consisting of:

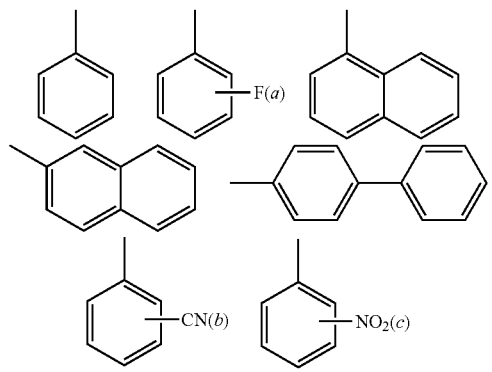

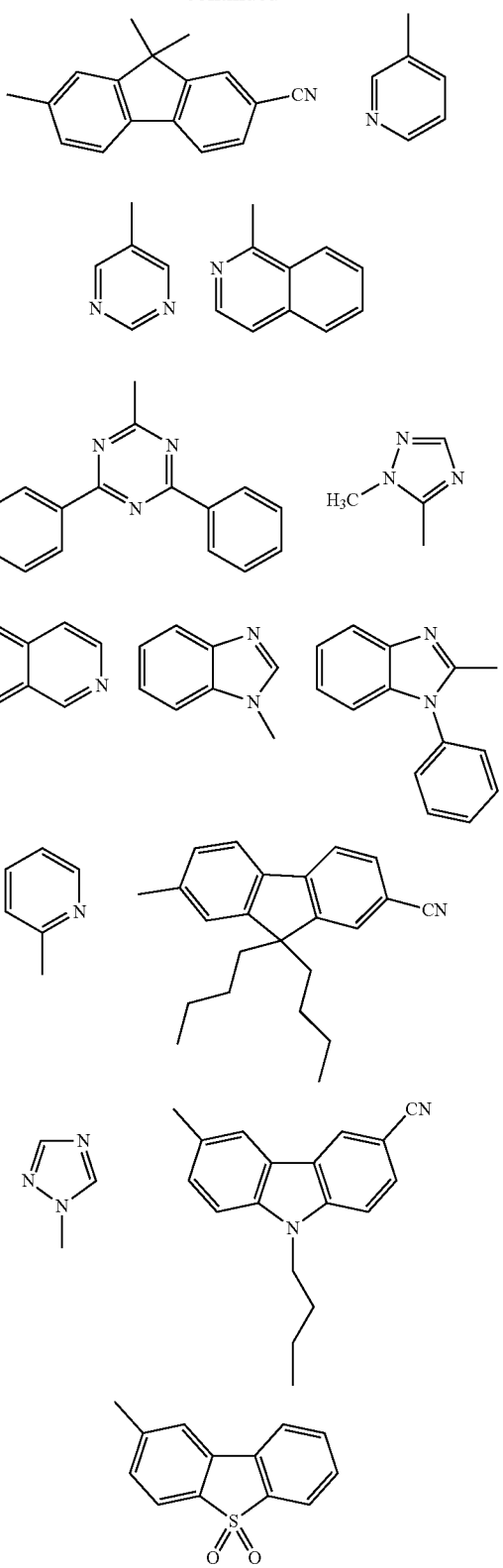

and —CN, in which a, b and c are respectively an integer independently selected from 1 to 5.

4. The compound according to claim 1, wherein the compound is expressed by formula (II),

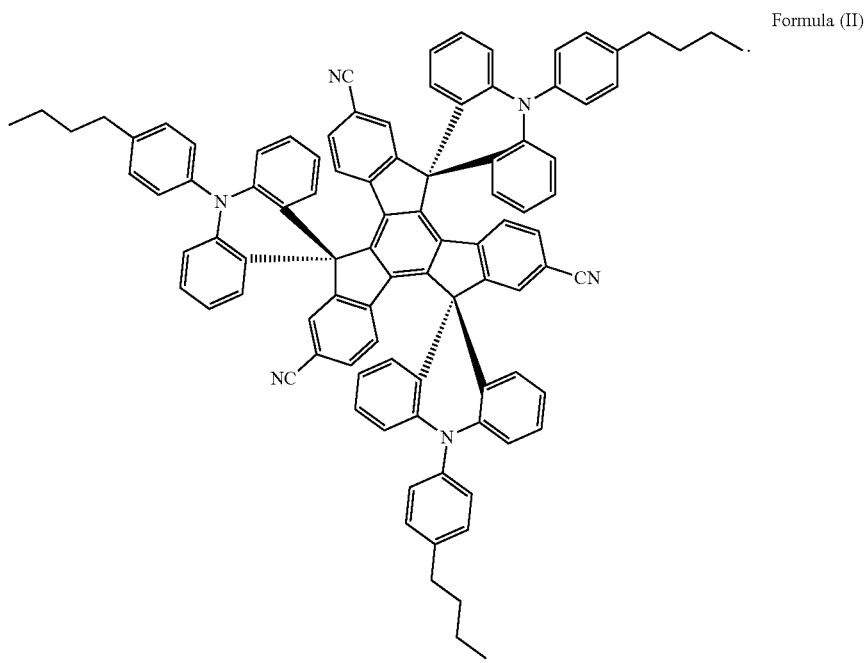 [SMILES: CCCCc1ccc(N2c3ccccc3[C@]3(c4cc(C#N)ccc4-c4c3c3c(c5c4[C@]4(c6cc(C#N)ccc6-5)c5ccccc5N(c5ccc(CCCC)cc5)c5ccccc54)[C@]4(c5cc(C#N)ccc5-3)c3ccccc3N(c3ccc(CCCC)cc3)c3ccccc34)c3ccccc32)cc1]

Formula (II)

5. A preparation method of the compound according to claim 1, comprising:
obtaining the compound expressed by formula (I) through a condensation reaction of a compound expressed by formula (III) and a compound expressed by formula (IV),

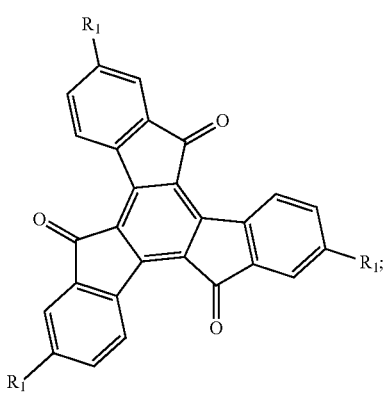

Formula (III)

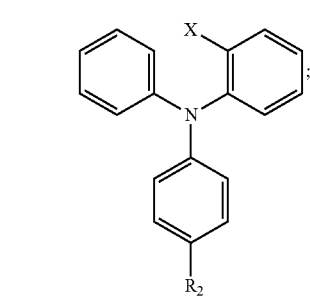

Formula (IV)

wherein X is any one selected from halogen.

6. The preparation method according to claim 5, wherein truxenone is prepared by using a raw material of 1,3-indandione, and the compound expressed by formula (III) is obtained through a substitution reaction with the truxenone as a reactant.

7. An organic light emitting display device, comprising an organic electroluminescent device comprising:
an organic functional layer, comprising one or more organic film layers, wherein at least one of the organic film layers is a light emitting layer;
the light emitting layer comprises a light emitting material, and the light emitting material comprises the compound according to claim 1.

8. The organic light emitting display device according to claim 7, wherein the organic electroluminescent device further comprises:
a base;
a first electrode arranged on the base; and
a second electrode arranged on the organic functional layer, wherein the organic functional layer is arranged on the first electrode.

9. The organic light emitting display device according to claim 7, wherein the light emitting material is a blue thermally activated delayed fluorescence material.

10. The organic light emitting display device according to claim 7, wherein the light emitting material is a host material or a guest material of the light emitting layer.

11. The organic light emitting display device according to claim 7, wherein the organic electroluminescent device is manufactured using a solution processing method.

12. The organic light emitting display device according to claim 11, wherein the solution processing method is selected from an ink-jet printing method.

* * * * *